US010506999B2

(12) United States Patent
Nishi et al.

(10) Patent No.: US 10,506,999 B2
(45) Date of Patent: Dec. 17, 2019

(54) RADIOGRAPHIC IMAGING DEVICE AND RADIOGRAPHY PROTECTION UNIT

(71) Applicant: FUJIFILM CORPORATION, Tokyo (JP)

(72) Inventors: Yoshihiro Nishi, Ashigarakami-gun (JP); Kenji Takata, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 446 days.

(21) Appl. No.: 14/334,803

(22) Filed: Jul. 18, 2014

(65) Prior Publication Data

US 2015/0025377 A1    Jan. 22, 2015

(30) Foreign Application Priority Data

Jul. 22, 2013   (JP) ................................ 2013-152072

(51) Int. Cl.
*A61B 6/00*   (2006.01)
*A61B 5/00*   (2006.01)
(Continued)

(52) U.S. Cl.
CPC .............. *A61B 6/502* (2013.01); *A61B 5/708* (2013.01); *A61B 6/025* (2013.01); *A61B 6/107* (2013.01); *A61B 6/0414* (2013.01); *A61B 6/0478* (2013.01)

(58) Field of Classification Search
CPC ......... A61B 6/502; A61B 6/025; A61B 6/107; A61B 5/708; A61B 6/0414; A61B 6/0478;
(Continued)

(56) References Cited

U.S. PATENT DOCUMENTS 5,340,171 A * 8/1994 Slaybuagh ............ E05B 47/023
                                                    292/201
6,310,355 B1 * 10/2001 Cadwalader ........... A61B 6/107
                                                    250/515.1
(Continued)

FOREIGN PATENT DOCUMENTS

CN    101535663 A   9/2009
JP    2006-231054 A  9/2006
(Continued)

OTHER PUBLICATIONS

Japanese Office Action, dated Nov. 17, 2015, in related application No. JP2013-152072.
(Continued)

*Primary Examiner* — Baisakhi Roy
*Assistant Examiner* — Patrick M Mehl
(74) *Attorney, Agent, or Firm* — Birch, Stewart, Kolasch & Birch, LLP

(57) ABSTRACT

A radiographic imaging device comprising an imaging platform that includes an imaging surface on which a breast of a test subject is to be rested; a radiation irradiation section disposed to face the imaging surface and irradiates radiation at the imaging surface; a main radiation protection portion that is disposed at the side of a region between the radiation irradiation section and the imaging surface and that is adapted to protect the test subject from the radiation; and an auxiliary radiation protection portion disposed at a side portion of the main radiation protection portion, and that is movable between a protecting position, at which the auxiliary radiation protection portion is adapted to protect the test subject, and a non-protecting position, at which the auxiliary radiation protection portion is withdrawn from the protecting position.

22 Claims, 28 Drawing Sheets

(51) Int. Cl.
*A61B 6/04* (2006.01)
*A61B 6/10* (2006.01)
*A61B 6/02* (2006.01)

(58) Field of Classification Search
CPC ..... G21F 7/00; G21F 7/02; G21F 7/03; G21F 7/04; G21F 7/041; G21F 7/06; G21F 7/062
See application file for complete search history.

(56) References Cited

U.S. PATENT DOCUMENTS

| | | | |
|---|---|---|---|
| 7,958,602 B2* | 6/2011 | Nishizawa | G06F 1/1681 16/367 |
| 2006/0055607 A1* | 3/2006 | Satoh | H01Q 1/084 343/702 |
| 2007/0242800 A1 | 10/2007 | Jing et al. | |
| 2009/0220055 A1 | 9/2009 | Nakata et al. | |
| 2010/0183119 A1* | 7/2010 | Ludwig | A61B 6/025 378/37 |
| 2012/0114095 A1* | 5/2012 | Smith | A61B 6/025 378/20 |
| 2013/0136239 A1* | 5/2013 | Laws | A61B 6/08 378/150 |
| 2013/0331682 A1 | 12/2013 | Ohta et al. | |

FOREIGN PATENT DOCUMENTS

| | | | | |
|---|---|---|---|---|
| JP | 2006231054 | * | 9/2006 | ............... A61B 6/00 |
| JP | 2006231054 A | * | 9/2006 | ............... A61B 6/00 |
| JP | 2007-50264 A | | 3/2007 | |
| JP | 2009-207561 A | | 9/2009 | |
| JP | 2012-175997 A | | 9/2012 | |

OTHER PUBLICATIONS

Office Action issued in corresponding Japan Application No. 2013-152072, dated Apr. 14, 2015, along with a partial English Translation.

Chinese Office Action, dated Feb. 11, 2018, for Chinese Application No. 201410347811.9, with English translation.

* cited by examiner

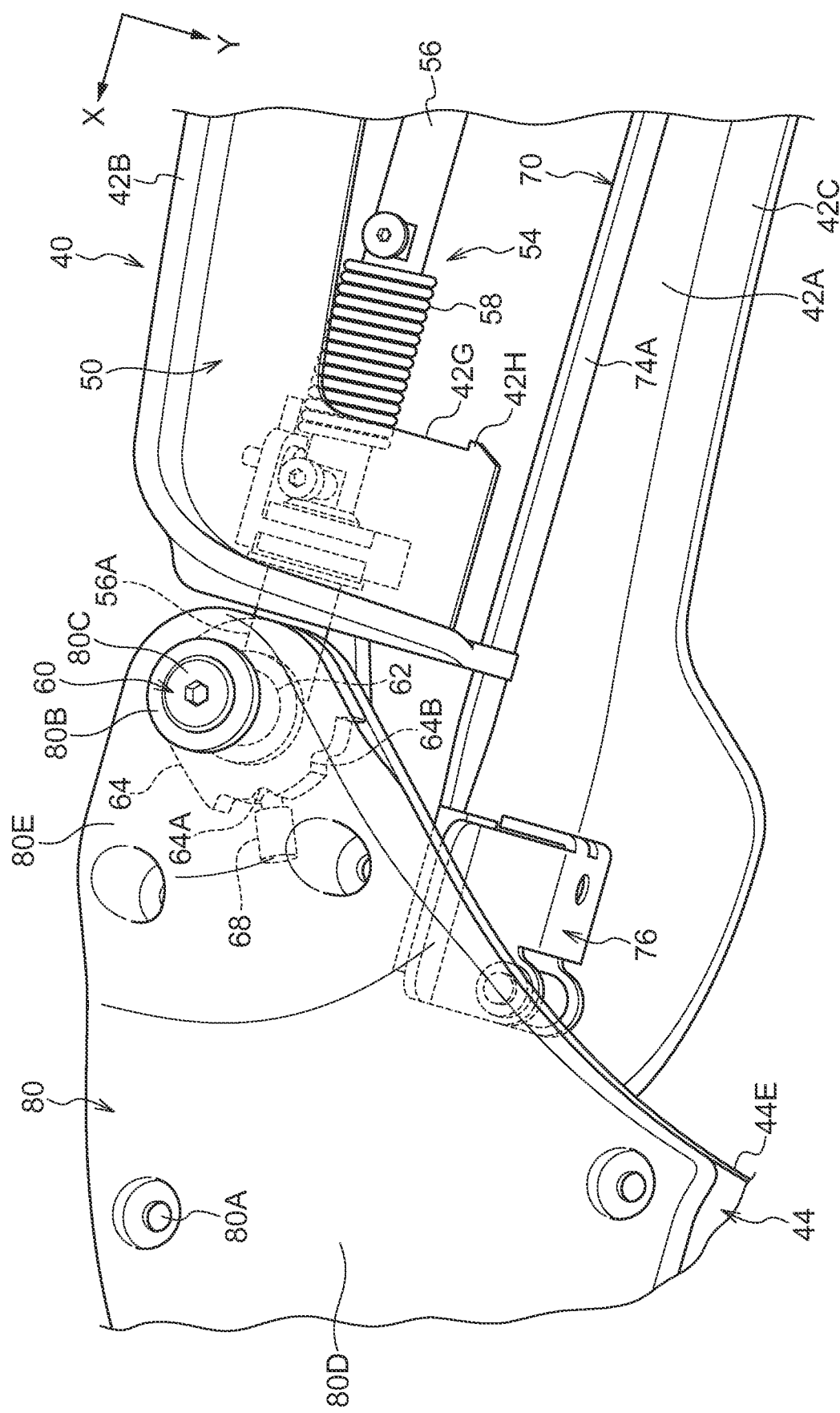

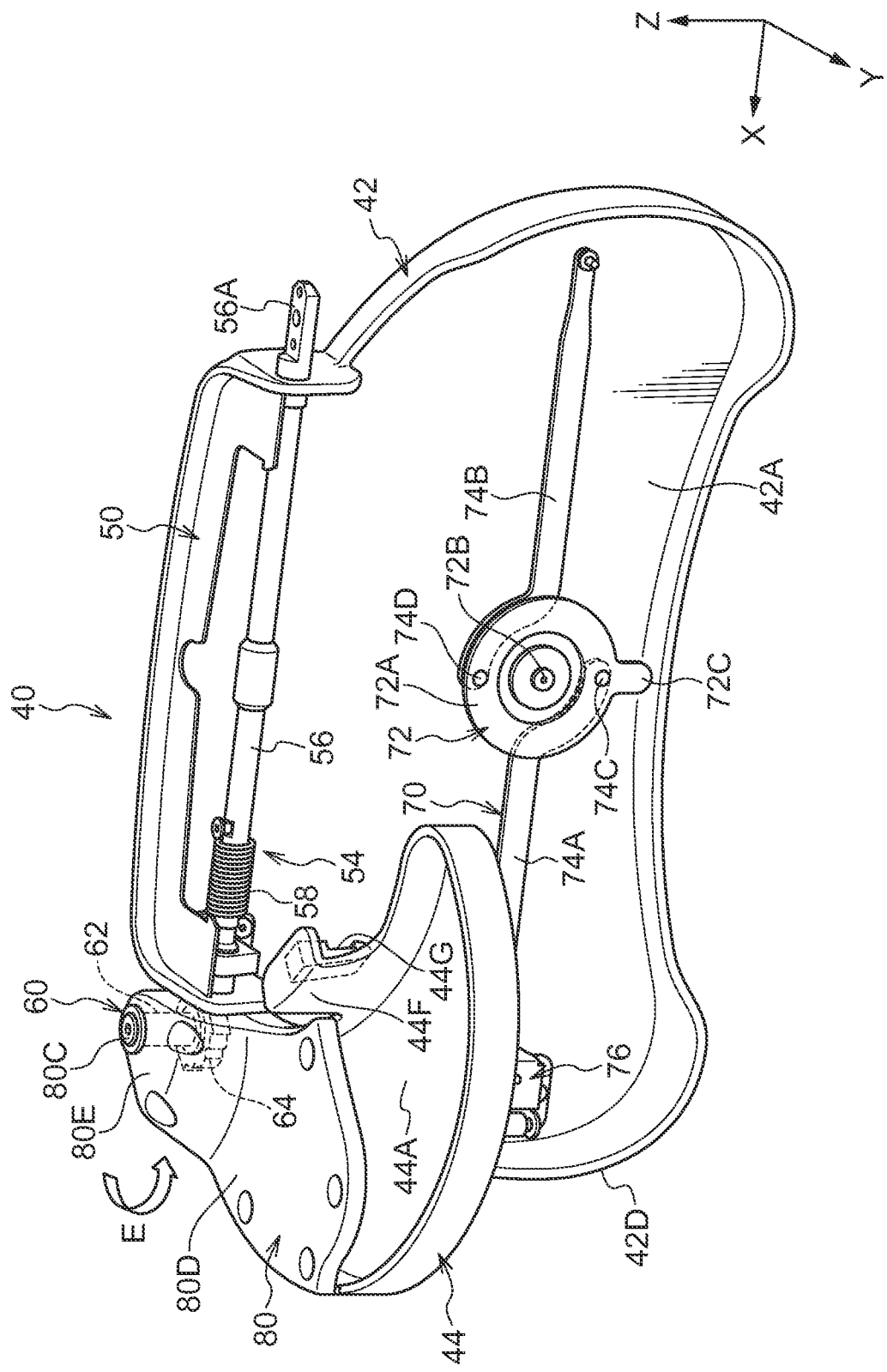

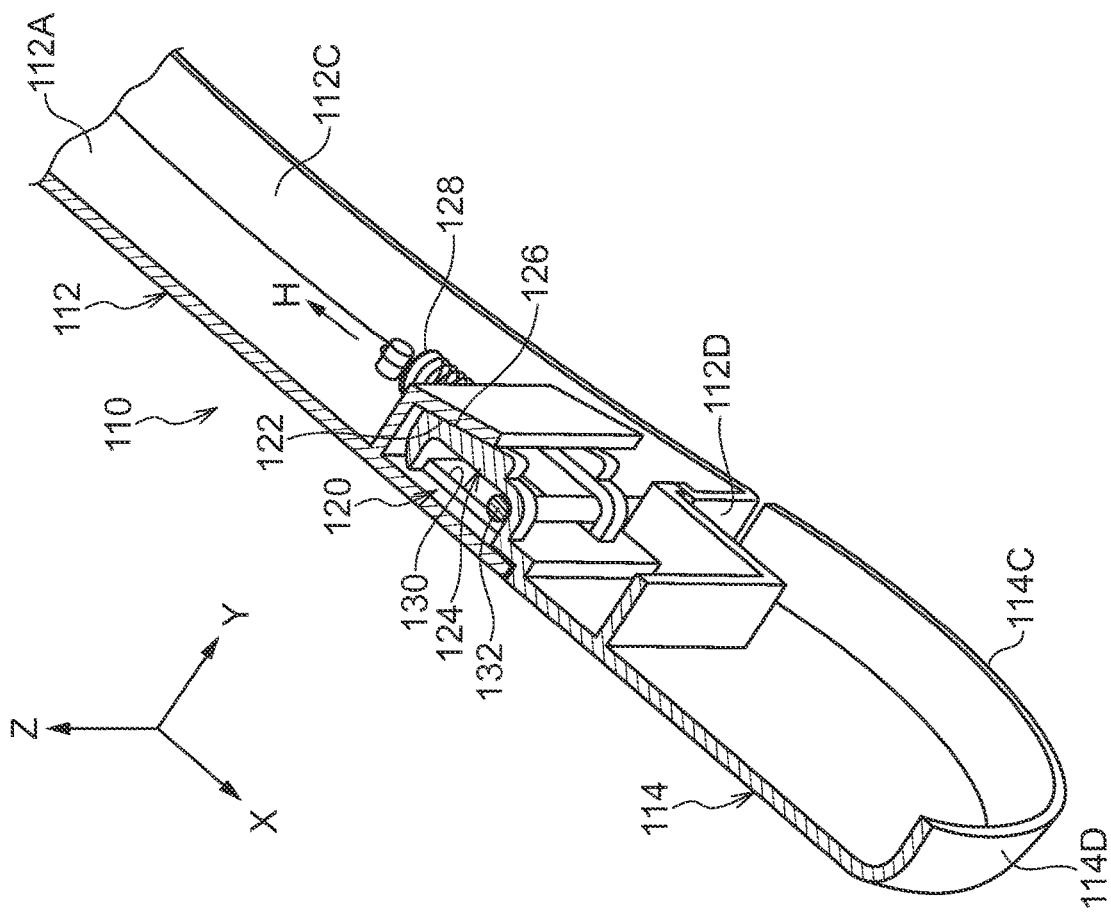

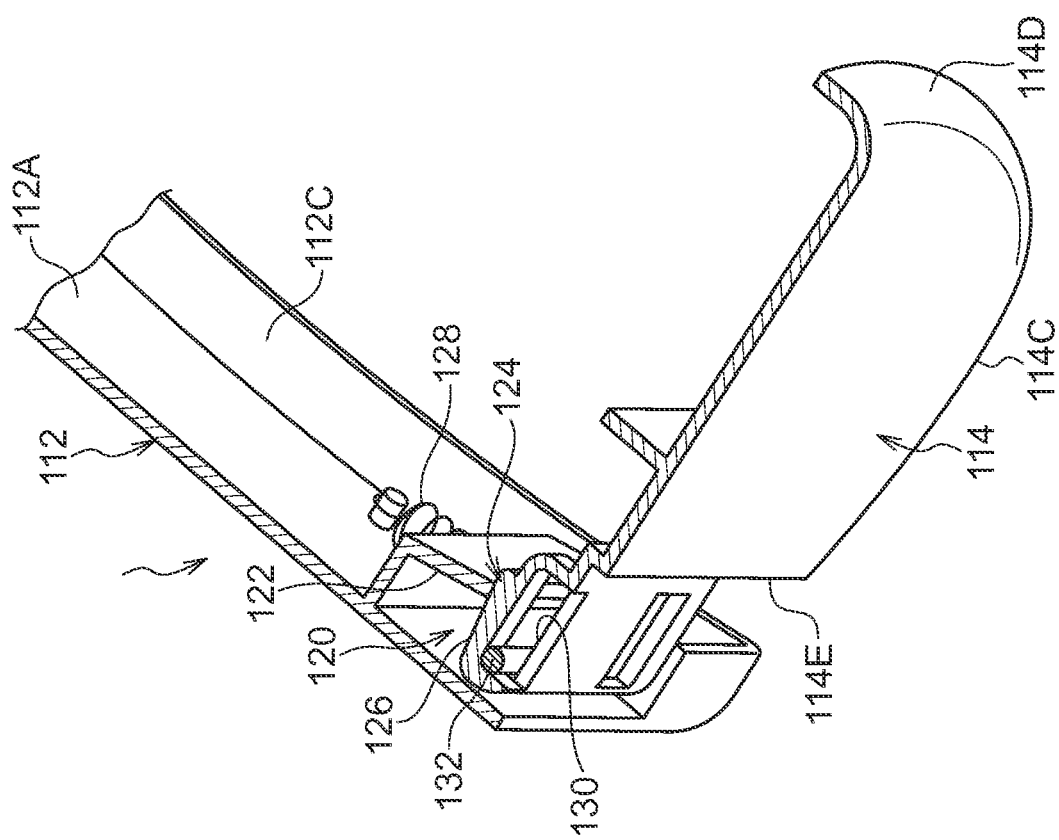

RADIOGRAPHIC IMAGING DEVICE AND RADIOGRAPHY PROTECTION UNIT

CROSS-REFERENCE TO RELATED APPLICATION

This application claims priority under 35 USC 119 from Japanese Patent Application, No. 2013-152072 filed on Jul. 22, 2013, the disclosure of which is incorporated by reference herein.

BACKGROUND OF THE INVENTION

Technical Field

The present invention relates to a radiographic imaging device and a radiography protection unit. The present invention particularly relates to a radiographic imaging device that serves as a mammography device that images radiographic images of the breasts of test subjects, and to a radiography protection unit that protects the test subjects from radiation.

Related Art

A mammography device whose purposes are early diagnosis of breast cancer and the like is known as a medical radio graphic imaging device. In a mammography device, the breast of a test subject is sandwiched between an imaging surface of an imaging platform and a compression plate. In a state in which the breast is compressed by the compression plate, a radiographic image is imaged. A radiation detection panel is incorporated in the imaging platform. Radiation irradiated from a radiation irradiation section passes through the breast and is detected at the radiation detection panel.

Mammography devices that include a face guard are disclosed in, for example, Japanese Patent Application Laid-Open (JP-A) Nos. 2009-207561 and 2007-50264. The face guard is mounted at the radiation irradiation section and is disposed between a radiation irradiation region and the test subject's face. The test subject's face is protected from radiation by the face guard.

SUMMARY

As is illustrated in the publications mentioned above, a mammography device is known that includes functions for performing both imaging from a vertical direction and imaging from diagonal directions. In particular, in a mammography device that includes a tomosynthesis function, the radiation irradiation section is turned to left and right relative to the test subject, and radiation images with differing irradiation angles centered on the breast are imaged. During tomosynthesis, the face guard is moved to left and right in association with the turning of the radiation irradiation section. As a result, depending on turning angles of the radiation irradiation section, the face guard may be displaced from a position corresponding with the test subject's face.

Accordingly, there has been progress in the development of a face guard whose length in the left-and-right direction is increased to enlarge the range of protection against radiation in accordance with a maximum turning angle of the radiation irradiation section. However, this enlarged face guard extends to the left and right more than necessary range of protection for usual imaging in which the tomosynthesis function is not used. Therefore, there has been room for the development of a radiography protection unit (a face guard) that provides appropriate protection ranges against radiation in accordance with imaging modes.

In consideration of the situation described above, the present invention provides a radiographic imaging device and radiography protection unit with which suitable setting of a range of protection against radiation may be performed with ease.

To address the subject described above, a radiographic imaging device relating to a first aspect of the present invention includes: an imaging platform that includes an imaging surface on which a breast of a test subject is to be rested; a radiation irradiation section that is disposed to face the imaging surface and irradiates radiation at the imaging surface; a main radiation protection portion that is disposed at the side of a region between the radiation irradiation section and the imaging surface at which side the test subject is disposed, and that is adapted to protect the test subject from the radiation; and an auxiliary radiation protection portion that is disposed at a side portion of the main radiation protection portion, and that is movable between a protecting position, at which the auxiliary radiation protection portion is adapted to protect the test subject, and a non-protecting position, at which the auxiliary radiation protection portion is withdrawn from the protecting position.

In the radiographic imaging device relating to the first aspect, the main radiation protection portion and the auxiliary radiation protection portion are provided. The main radiation protection portion is disposed at the test subject side of the region between the imaging platform and the radiation irradiation section, and the test subject is protected from radiation by this main radiation protection portion. Meanwhile, the auxiliary radiation protection portion is disposed at the side portion of the main radiation protection portion.

The auxiliary radiation protection portion is structured to be movable between the protecting position and the non-protecting position that is withdrawn from the protecting position. Consequently, when the auxiliary radiation protection portion is at the protecting position, a range in which the radiation is shielded by the main radiation protection portion and the auxiliary radiation protection portion is expanded, and thus the range of protection from radiation is enlarged. In contrast, when the auxiliary radiation protection portion is withdrawn from the protecting position to the non-protecting position, the radiation is shielded only by the main radiation protection portion, and thus the range of protection from radiation is reduced.

In a radiographic imaging device relating to a second aspect, in the radiographic imaging device relating to the first aspect, the auxiliary radiation protection portion is movable between the non-protecting position, which is at a rearward side that is the opposite side of the main radiation protection portion from the side thereof at which the test subject is disposed, and the protecting position, which is at the side portion of the main radiation protection portion at the side at which the test subject is disposed.

According to the radiographic imaging device relating to the second aspect, the auxiliary radiation protection portion is structured to be movable between the non-protecting position at the rearward side of the main radiation protection portion and the protecting position. Thus, when the auxiliary radiation protection portion has been withdrawn from the protecting position to the non-protecting position, the auxiliary radiation protection portion is stowed at the rearward side of the main radiation protection portion. Therefore, stowing of the auxiliary radiation protection portion can be excellently conducted when the range of protection against radiation is reduced.

In a radiographic imaging device relating to a third aspect, in the radiographic imaging device relating to the first aspect or the second aspect, a first turning shaft is provided at the side portion, an axial direction of the first turning shaft being a direction along an upper edge of the main radiation protection portion, and the auxiliary radiation protection portion turns about the first turning shaft between the protecting position and the non-protecting position.

According to the radiographic imaging device relating to the third aspect, the auxiliary radiation protection portion is structured to turn about the first turning shaft that is provided at the side portion of the main radiation protection portion. The axial direction of the first turning shaft is in the direction along the upper edge of the main radiation protection portion, which is, for example, a horizontal direction. Therefore, the auxiliary radiation protection portion can be moved between the protecting position and the non-protecting position just by being turned relative to the main radiation protection portion.

In a radiographic imaging device relating to a fourth aspect, in the radiographic imaging device relating to the third aspect, a second turning shaft is provided at the first turning shaft, an axial direction of the second turning shaft being a direction that intersects the first turning shaft, and the auxiliary radiation protection portion turns about the second turning shaft between the non-protecting position and a stowed position, which is at a rear face side of the main radiation protection portion relative to the non-protecting position.

According to the radiographic imaging device relating to the fourth aspect, the auxiliary radiation protection portion is structured to also turn about the second turning shaft that is provided at the first turning shaft. Thus, the auxiliary radiation protection portion that has been moved from the protecting position to the non-protecting position can be moved between the non-protecting position and the stowed position at the rear face side of the main radiation protection portion. Therefore, stowing of the auxiliary radiation protection portion can be excellently performed furthermore when the range of protection against radiation is reduced.

In a radiographic imaging device relating to a fifth aspect, the radiographic imaging device relating to the fourth aspect further includes: a first resilient member that applies a turning force, from the protecting position of the auxiliary radiation protection portion toward the non-protecting position, to the first turning shaft; and a retention and release mechanism that is capable of retaining the auxiliary radiation protection portion at the protecting position at the side portion in opposition to the turning force and is capable of releasing this retention.

In the radiographic imaging device relating to the fifth aspect, the first resilient member and the retention and release mechanism are provided. The turning force, from the protecting position of the auxiliary radiation protection portion to the non-protecting position, is applied to the first turning shaft by the first resilient member. The auxiliary radiation protection portion is retained at the protecting position at the side portion of the main radiation protection portion, in opposition to the turning force from the first resilient member, by the retention and release mechanism, and this retention can be released by the retention and release mechanism. Thus, when the retention by the retention and release mechanism is released, the auxiliary radiation protection portion is automatically turned from the protecting position to the non-protecting position by the turning force applied to the first turning shaft by the first resilient member. Therefore, an operation to reduce the region of protection against radiation from the enlarged state may be performed automatically.

In a radiographic imaging device relating to a sixth aspect, the radiographic imaging device relating to the fourth aspect or the fifth aspect further includes a turning position retention mechanism that retains a turning position of the auxiliary radiation protection portion at each of the non-protecting position and the stowed position.

In the radiographic imaging device relating to the sixth aspect, the turning position retention mechanism is provided, and respective turning positions of the auxiliary radiation protection portion at the non-protecting position and the stowed position are retained by the turning position retention mechanism. Thus, the auxiliary radiation protection portion may be immediately and reliably retained at each of the non-protecting position and the stowed position. Therefore, the operation to reduce the range of protection against radiation and an operation of stowing the auxiliary radiation protection portion may be performed reliably.

In a radiographic imaging device relating to a seventh aspect, in the radiographic imaging device relating to any one of the first to sixth aspects, the auxiliary radiation protection portion includes: a plate-shaped protection portion main body; and a reinforcing member that reinforces a joining location between the protection portion main body and the first turning shaft.

According to the radiographic imaging device relating to the seventh aspect, the auxiliary radiation protection portion is provided with the protection portion main body and the reinforcing member. The joining location between the protection portion main body and the first turning shaft is reinforced by the reinforcing member. Therefore, stiffness of the auxiliary radiation protection portion may be improved.

In a radiographic imaging device relating to an eighth aspect, in the radiographic imaging device relating to the first aspect or the second aspect, a third turning shaft is provided at the side portion of the main radiation protection portion, an axial direction of the third turning shaft being a direction along an irradiation axis of the radiation, and the auxiliary radiation protection portion turns about the third turning shaft between the protecting position and the non-protecting position.

According to the radiographic imaging device relating to the eighth aspect, the auxiliary radiation protection portion is structured to turn about the third turning shaft that is provided at the side portion of the main radiation protection portion. The axial direction of the third turning shaft is a direction along an irradiation axis of the radiation, for example, a vertical direction. Therefore, the auxiliary radiation protection portion can be moved between the protecting position and the non-protecting position just by being turned relative to the main radiation protection portion.

In a radiographic imaging device relating to a ninth aspect, in the radiographic imaging device relating to the eighth aspect, the auxiliary radiation protection portion folds from the protecting position, which is at the side portion of the main radiation protection portion at the side at which the test subject is disposed, to the non-protecting position, at which the auxiliary radiation protection portion is disposed at the rearward side of the main radiation protection portion.

According to the radiographic imaging device relating to the ninth aspect, the auxiliary radiation protection portion has a folding structure at the side portion of the main radiation protection portion. Therefore, the auxiliary radiation protection portion can be moved between the protecting position and the non-protecting position simply by being folded relative to the main radiation protection portion.

In a radiographic imaging device relating to a tenth aspect, the radiographic imaging device relating to the eighth aspect or the ninth aspect further includes: a turning engagement portion that is provided at the auxiliary radiation protection portion, engages with the third turning shaft when the auxiliary radiation protection portion is moved from the protecting position in a planar direction of the main radiation protection portion, and allows turning of the auxiliary radiation protection portion toward the non-protecting position; a guiding portion that is provided at the side portion and that guides the turning engagement portion in the planar direction; a guided portion that is provided at the turning engagement portion and that touches and is guided by the guiding portion when the auxiliary radiation protection portion is moved in the planar direction; and a second resilient member that urges the guided portion in a direction causing the guided portion to touch the guiding portion.

In the radiographic imaging device relating to the tenth aspect, the turning engagement portion is provided at the auxiliary radiation protection portion. When the auxiliary radiation protection portion is moved from the protecting position in the planar direction of the main radiation protection portion, the turning engagement portion engages with the third turning shaft, and the auxiliary radiation protection portion may be turned to the non-protecting position. The guiding portion is provided at the side portion of the main radiation protection portion, and guides the turning engagement portion along the planar direction. The guided portion is provided at the turning engagement portion. When the auxiliary radiation protection portion is moved in the planar direction, the guided portion touches against and is guided by the guiding portion. The second resilient member is also provided, which guides the guided portion in the direction in which the guided portion is touched against the guiding portion. Therefore, when the auxiliary radiation protection portion is at the protecting position, the second resilient member is urged in the direction in which the guided portion is touched against the guiding portion, and looseness between the guiding portion and the guided portion is effectively reduced. Thus, the auxiliary radiation protection portion may be securely retained at the main radiation protection portion.

In a radiographic imaging device relating to an eleventh aspect, in the radiographic imaging device relating to any one of the first to tenth aspects, the auxiliary radiation protection portion is provided at each of two side portions of the main radiation protection portion.

According to the radiographic imaging device relating to the eleventh aspect, the auxiliary radiation protection portion is provided at both side portions of the main radiation protection portion. Therefore, the range of protection against radiation can be enlarged further.

In a radiographic imaging device relating to a twelfth aspect, in the radiographic imaging device relating to any one of the first to eleventh aspects, the main radiation protection portion is detachably provided at a lower end portion of the radiation irradiation section.

According to the radiographic imaging device relating to the twelfth aspect, the main radiation protection portion is detachably provided at the lower end portion of the radiation irradiation section. Thus, a radiography protection unit including the main radiation protection portion and the auxiliary radiation protection portion can be mounted and dismounted with ease.

In a radiographic imaging device relating to a thirteenth aspect, in the radiographic imaging device relating to any one of the first to twelfth aspects, as viewed from the side at which the test subject is disposed, a boundary location between the main radiation protection portion and the auxiliary radiation protection portion is specified to be between an irradiation region of the radiation and a side face of the radiation irradiation section.

According to the radiographic imaging device relating to the thirteenth aspect, the boundary location between the main radiation protection portion and the auxiliary radiation protection portion is specified to be at the side of the irradiation region of the radiation at which the side face of the radiation irradiation section is disposed. Thus, the range of protection against radiation may be assured. Meanwhile, because the boundary location is specified to be at the radiation irradiation region side relative to the side portion of the radiation irradiation section and the auxiliary radiation protection portion is stowed to the irradiation region side, a space for stowing the auxiliary radiation protection portion at the non-protecting position can be saved.

A radiography protection unit relating to a fourteenth aspect includes: the main radiation protection portion and the auxiliary radiation protection portion both of which are provided in a radiographic imaging device relating to any one of the first to thirteenth aspects and the auxiliary radiation protection portion is provided at the side portion of the main radiation protection portion.

With the radiography protection unit relating to the fourteenth aspect, the radiographic imaging device relating to any one of the first to thirteenth aspects may be realized.

The radiographic imaging device and radiography protection unit according to the present invention have an excellent effect in that a range of protection against radiation may be suitably specified with ease.

BRIEF DESCRIPTION OF THE DRAWINGS

Embodiments of the present invention will be described in detail based on the following figures, wherein:

FIG. 8 is a magnified perspective view of the principal portions of the radiography protection unit shown in FIG. 7;

FIG. 9 is a perspective view, corresponding to FIG. 5, of the radiography protection unit when the auxiliary radiation protection portion is at a stowed position;

FIG. 10A is a perspective view of principal portions when the auxiliary radiation protection portions are at protecting positions, viewed from a little to the right at the test subject side; FIG. 10B is a perspective view of the principal portions, corresponding to FIG. 10A, when the auxiliary radiation protection portions are at the non-protecting positions thereof; and FIG. 10C is a perspective view of the principal portions, corresponding to FIG. 10A, when the auxiliary radiation protection portions are at the stowed positions thereof;

FIG. 24A is a perspective view of the principal portions when the auxiliary radiation protection portions are at the protecting positions, viewed from a little to the right at the test subject side; FIG. 24B is a perspective view of the principal portions, corresponding to FIG. 24A, when the auxiliary radiation protection portions are being withdrawn from the protecting positions and moved to the non-protecting positions; and FIG. 24C is a perspective view of the principal portions, corresponding to FIG. 24A, when the auxiliary radiation protection portions are at the non-protecting positions;

FIG. 25A is a diagram describing a moving mechanism of the radiography protection unit shown in FIG. 21, and is a plan-section perspective diagram of principal portions viewed from above at the rearward of the right side, when the auxiliary radiation protection portion is at the protecting position; and FIG. 25B is a plan-section perspective diagram of the principal portions, corresponding to FIG. 25A, when the auxiliary radiation protection portion is at the non-protecting position.

DETAILED DESCRIPTION OF THE INVENTION

Figure 1:
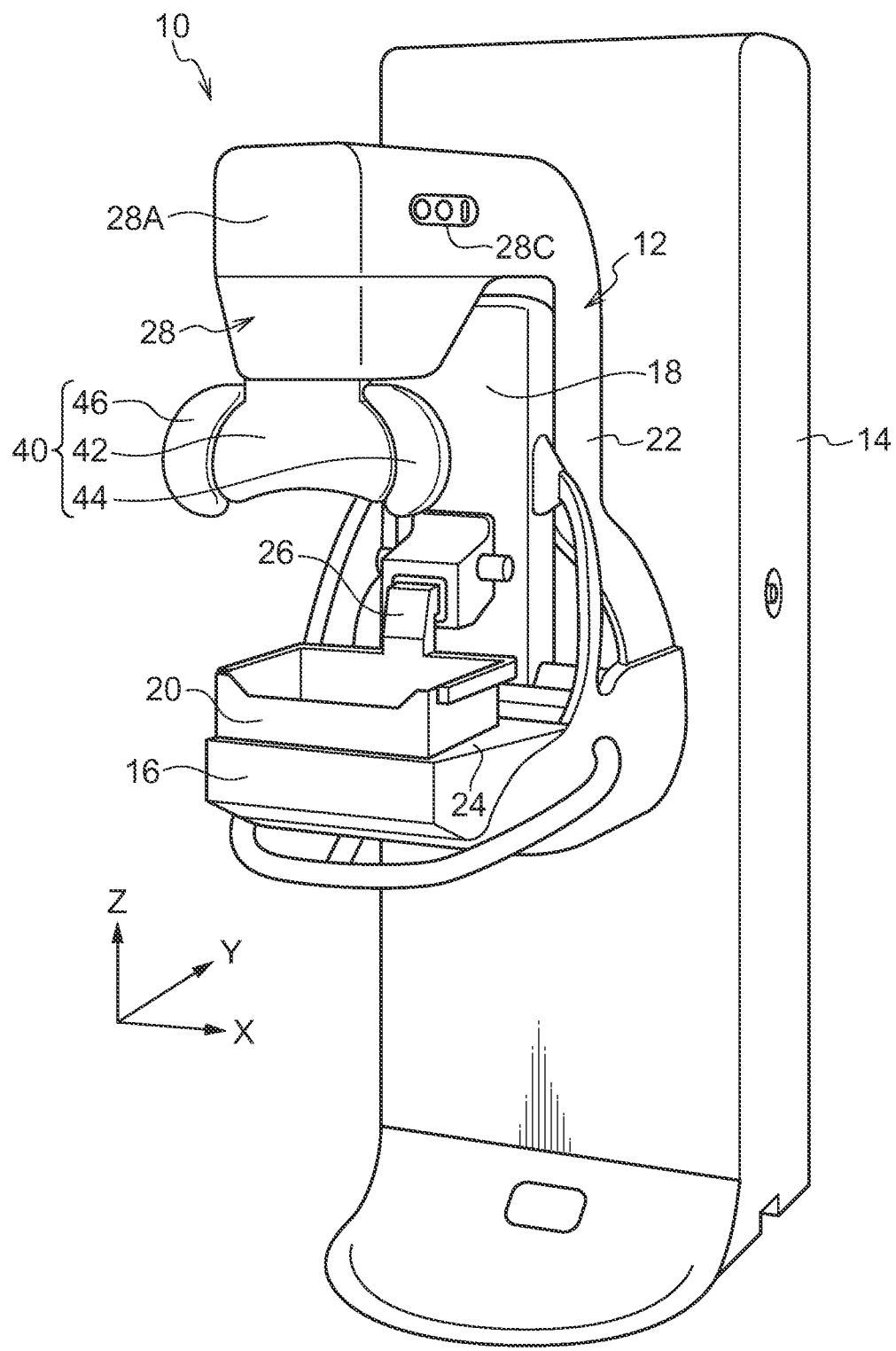
FIG. 1 is a perspective view of the overall structure of a radiographic imaging device in accordance with a first exemplary embodiment of the present invention, viewed from a little to the right at a test subject side (thoracic wall side)

Herebelow, exemplary embodiments relating to the present invention are described while referring to the attached drawings. Herein, structural elements with the same functions are assigned the same reference symbols in the drawings, and duplicative descriptions are omitted as appropriate. The direction marked with the reference symbol X that is shown as appropriate in the drawings indicates a direction from a left side to a right side as viewed from a test subject side (a thoracic wall side) in a state in which the test subject is facing a radiographic imaging device for imaging. The direction marked with the reference symbol Y indicates a direction from a front face at the test subject side toward a rear face side of the radiographic imaging device, and the direction marked with the reference symbol Z indicates a direction from a lower side at the legs of the test subject toward upper side of the radiographic imaging device. In other words, the reference symbols X, Y and Z are directions matching an X-axis direction, a Y-axis direction and a Z-axis direction of an XYZ coordinate system.

First Exemplary Embodiment

A first exemplary embodiment of the present invention is described using FIG. 1 to FIG. 14. The first exemplary embodiment describes an example in which the present invention is applied to a radiographic imaging device that is a mammography device including a tomosynthesis imaging function.

—Overall Structure of the Radiographic Imaging Device—

As shown in FIG. 1, a radiographic imaging device (mammography device) 10 in accordance with the first exemplary embodiment images the breasts of a test subject in an upright posture with an image based on an irradiation of radiation. The radiographic imaging device 10 may image separate left and right images of the breasts of a test subject in a sitting posture, who is seated on a chair such as, for example, a wheelchair, or a test subject of whom only the upper body is in the upright posture.

The radiographic imaging device 10 is equipped with an imaging section 12 and a pedestal section 14. The imaging section 12 is disposed at a front face side of the radiographic imaging device 10 (the side at which the thoracic wall of the test subject is disposed) and is formed substantially in a "C" shape in side view. The pedestal section 14 is disposed at a rear face side (the Y direction side) relative to the imaging section 12, and supports the imaging section 12 from the rear face side thereof. The imaging section 12 is equipped, in a direction from the lower side to the upper side (in the Z direction), with an imaging platform 16, a retention portion 18, a compression plate 20 and a support section 22. An imaging surface 24 is provided at an uppermost portion of the imaging platform 16. The breast of the test subject may be placed on (abutted against) the imaging surface 24. The shape of the imaging surface 24 is not particularly limited but in this case the shape of the imaging surface 24 in a plan view is a trapezoid shape that widens a little from the thoracic wall side toward the rear face side. With a view point of transmissibility of radiation and mechanical strength, at least the imaging surface 24 is formed of, for example, a carbon fiber-reinforced plastic. The imaging platform 16 is supported at the lower side of the retention portion 18. The compression plate 20 is supported, via a support arm 26, at the upper side of the retention portion 18 relative to the imaging platform 16.

The compression plate 20 is movable in the vertical direction (the Z direction) relative to the imaging surface 24, and sandwiches the breast against the imaging surface 24, compressing the breast down from above. The compression plate 20 is structured by, for example, a square shaft with a base, which is hollow and opens upward. A material used for the compression plate 20 is a thermoplastic resin that, more specifically described, is a polycarbonate, an ABS resin (a synthetic copolymer resin of acrylonitrile, butadiene and styrene) or the like. A lid member that covers the opening of the compression plate 20 may be provided in the first exemplary embodiment but need not particularly be provided. A turning shaft whose axial direction is in the X direction, which shaft is not shown in the drawings, is provided at the support arm 26. This turning shaft is capable of adjusting a compression angle of the compression plate 20 about a center of turning of the shaft.

Figure 14:
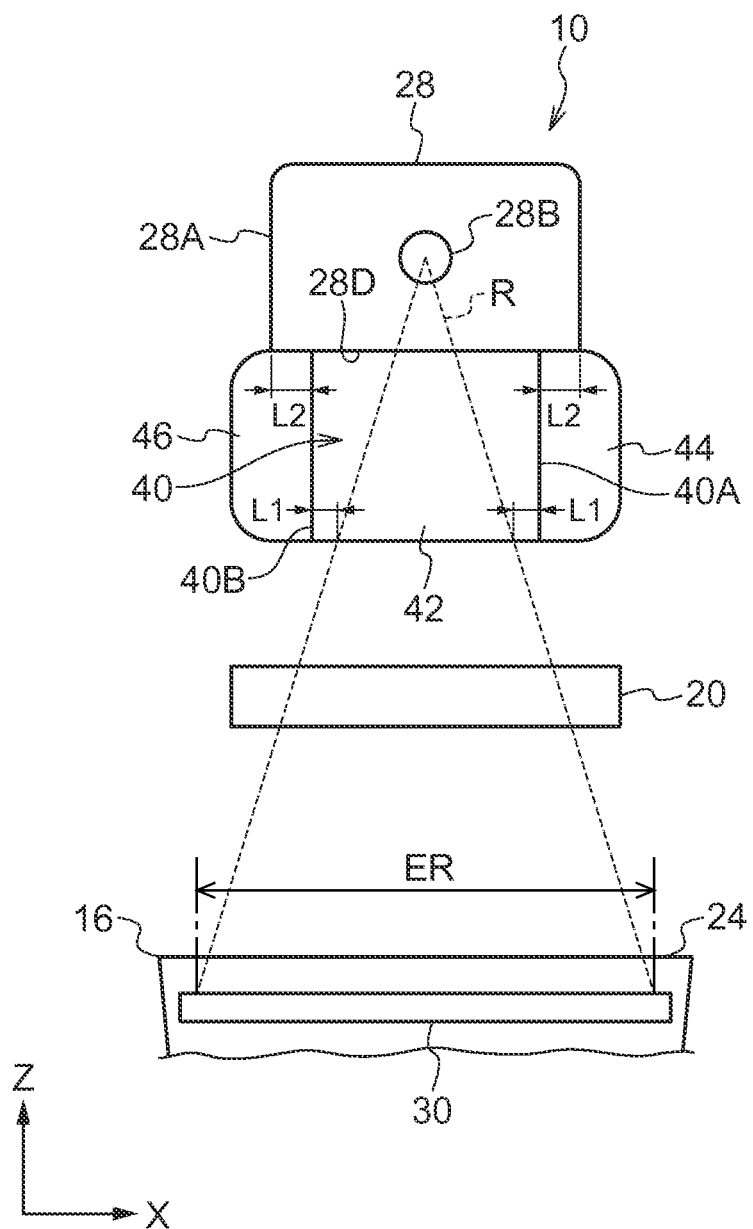
FIG. 14 is a schematic front view of principal portions of a radiographic imaging device, describing positional relationships between a main radiation protection portion and the auxiliary radiation protection portions of a radiography protection unit in accordance with a first variant example of the first exemplary embodiment.

The support section 22 is provided at the rear face side of the retention portion 18 as a separate structural element from the retention portion 18. The support section 22 is formed substantially in an inverted "L" shape in side view. A radiation irradiation section 28 is provided at an upper portion of the support section 22. The radiation irradiation section 28 is capable of irradiating radiation for imaging or for measurement toward the imaging surface 24. In the radiographic imaging device 10 according to the present exemplary embodiment, as shown in FIG. 14, a radiation generation source 28B is provided inside a casing 28A of the radiation irradiation section 28, and X-rays are generated by the radiation generation source 28B to serve as the radiation. A control section 28C is disposed at a side face of the casing 28A of the radiation irradiation section 28. Note that the present invention is not limited to X-rays. The radiation that is used may be, for example, gamma rays that are used at least for clinical purposes, an electron beam, a neutron beam, a proton beam, a baryon beam or the like.

As shown in FIG. 14, a radiation detection panel 30 that serves as a radiation detector is provided inside the imaging platform 16, facing and separated from the radiation irradiation section 28. The radiation detection panel 30 senses an irradiation of radiation from the radiation irradiation section 28, which has passed through the compression plate 20, the breast and the imaging surface 24 and carries image information of the breast, and detects the image information.

Returning to FIG. 1, a turning shaft whose axial direction is in the Y direction toward the front face side, which shaft is not shown in the drawings, is provided at an up-and-down direction middle portion of the pedestal section 14. At least the support section 22 is axially supported at this turning shaft to be turnable. Thus, the imaging section 12, including the support section 22, is made turnable relative to the pedestal section 14 about the turning shaft, to left and right (clockwise and counterclockwise) as viewed from the test subject side. The radiographic imaging device 10 is made capable of tomosynthesis imaging by this structure.

—Structure of the Radiography Protection Unit—

Figure 2:
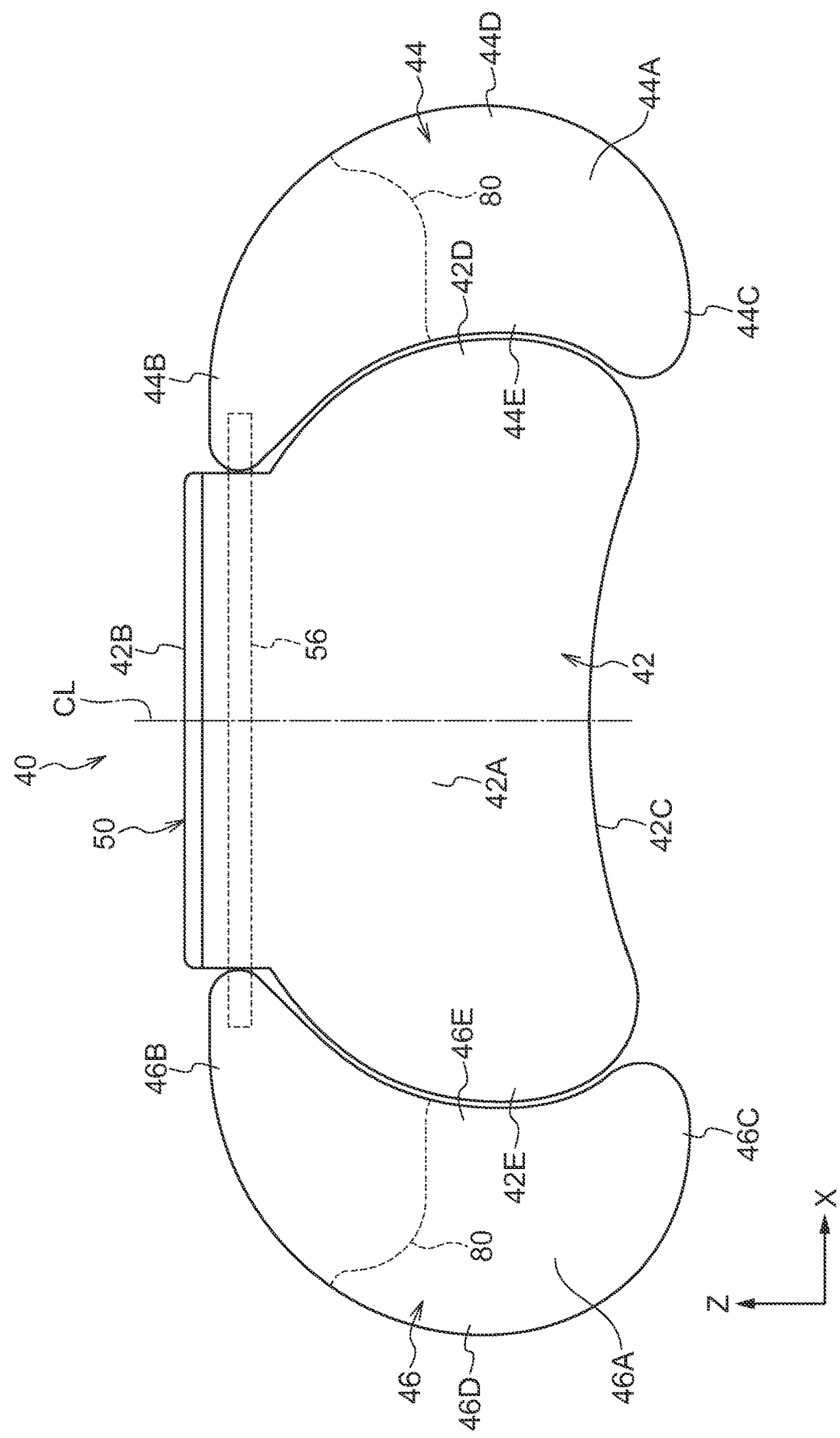
FIG. 2 is a front view of the overall structure of a radiography protection unit that is provided at the radiographic imaging device shown in FIG. 1, viewed from the test subject side.

As shown in FIG. 1 and FIG. 2, the radiographic imaging device 10 is equipped with a radiography protection unit 40 at the test subject side (the thoracic wall side) of the region between the radiation irradiation section 28 and the imaging surface 24. The radiography protection unit 40 protects, in particular, the face of the test subject against the radiation when a radiographic image of the breast(s) of the test subject is being imaged. The radiography protection unit 40 is provided with a main radiation protection portion 42 and auxiliary radiation protection portions 44 and 46. The auxiliary radiation protection portion 44 is disposed at a side portion 42D at the right side of the main radiation protection portion 42 as viewed from the test subject side, and the auxiliary radiation protection portion 46 is disposed at a side portion 42E at the left side of the main radiation protection portion 42.

—Structure of the Main Radiation Protection Portion—

Figure 3:
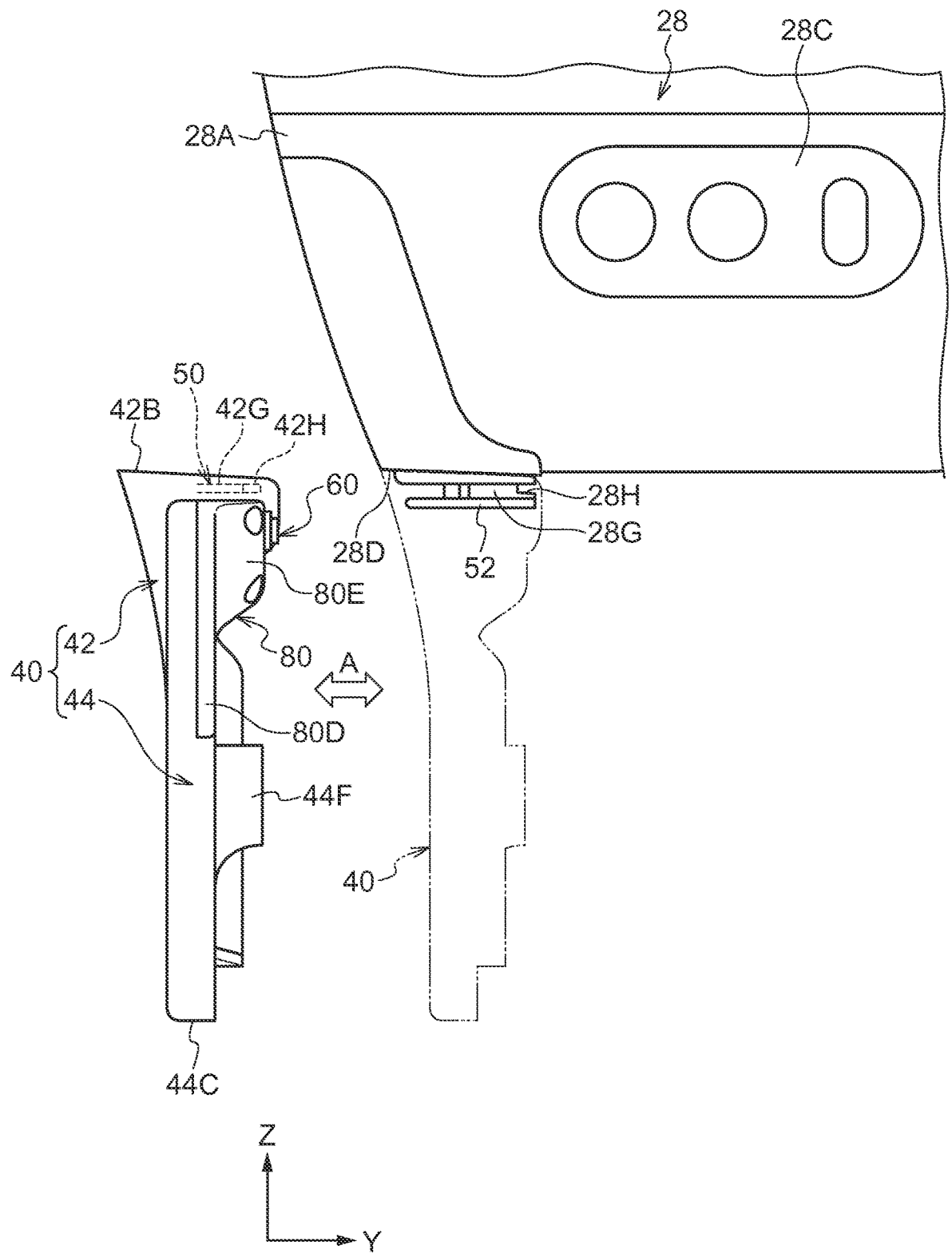
FIG. 3 is a side view showing a state of mounting of the radiography protection unit at a radiation irradiation section of the radiographic imaging device shown in FIG. 1.

The main radiation protection portion 42 of the radiography protection unit 40, as shown in FIG. 2, is disposed at the front face side (the thoracic wall side) of a floor face 28D of the radiation irradiation section 28 (see FIG. 3). In the first exemplary embodiment, the main radiation protection portion 42 is provided with a protection portion main body 42A that is formed by a plate member, a length direction of which is in the left-and-right direction (the X direction) as viewed from the test subject side. An upper portion 42B of the protection portion main body 42A is formed in a protruding shape. An upper face of the upper portion 42B is formed in a flat shape in the horizontal direction, to match the shape of the floor face 28D of the radiation irradiation section 28. A lower portion 42C that is opposite from the upper portion 42B includes a curved shape that is recessed upward. In the first exemplary embodiment, a radius of curvature of this curve is equal to a perpendicular length from a midpoint of the lower portion 42C (the point of intersection in FIG. 2 between the lower portion 42C and a center line CL) to the imaging surface 24. Described more specifically, the curve has a shape that substantially matches a curve that the lower portion 42C describes in turning clockwise or counterclockwise during tomosynthesis imaging (see FIG. 11 to FIG. 13). The side portion 42D at the right side is formed in a curved shape that protrudes to the right side. The side portion 42E at the left side is formed in a curved shape that protrudes to the left side, in mirror symmetry with the side portion 42D. Respective end portions of the lower portion 42C, the side portion 42D and the side portion 42E are not assigned particular reference symbols but, as illustrated by the example in FIG. 5, these end portions are structured as a rib that is inflected to the rear face side, improving the mechanical strength of the protection portion main body 42A.

In the first exemplary embodiment, the protection portion main body 42A is formed of the same material as the material of the compression plate 20, preferably a thermoplastic resin that is a polycarbonate. In this case, the protection portion main body 42A is fabricated by, for example, extrusion molding. A surface treatment that improves smoothness against the test subject's face is applied at least to a portion of the protection portion main body 42A that abuts against the face (the skin) of the test subject, in this case to the whole of the test subject side of the protection portion main body 42A. A blasting treatment that roughens the surface and reduces a contact area with the face can be used as this surface treatment. Another surface treatment that may be used is a coating treatment that applies, for example, a silicone resin, TEFLON (registered trademark) or the like to the surface of the protection portion main body 42A to improve smoothness.

—Structure of the Auxiliary Radiation Protection Portion—

As shown in FIG. 2, the auxiliary radiation protection portion 44 is a structure that enlarges a range of protection against radiation of the main radiation protection portion 42 further to the right side as viewed from the test subject side. The auxiliary radiation protection portion 44 is provided with a protection portion main body 44A that is formed of a plate member in a crescent moon shape. The right side of the protection portion main body 44A is formed in a curved shape that protrudes to the outer side between an upper portion 44B and a lower portion 44C, which faces the upper portion 44B with a right side (outer side) portion 44D therebetween. A side portion 44E at the left side (inner side) of the protection portion main body 44A is formed in a curved shape that is recessed. Respective end portions of the upper portion 44B, the lower portion 44C, the side portion 44D and the side portion 44E of the protection portion main body 44A are not assigned particular reference symbols but, as illustrated by the example in FIG. 5, these end portions are structured as a rib that is inflected to the rear face side, improving the mechanical strength of the protection portion main body 44A.

Meanwhile, the auxiliary radiation protection portion 46 is a structure that enlarges the range of protection against radiation of the main radiation protection portion 42 further to the left side. The auxiliary radiation protection portion 46 is formed in a shape with mirror symmetry with the auxiliary radiation protection portion 44 about the center line CL, which is drawn for convenience extending in the up-and-down direction through the center, in the left-and-right direction, of the main radiation protection portion 42. Thus, the auxiliary radiation protection portion 46 is provided with a protection portion main body 46A that is formed of a plate material in a crescent moon shape, similarly to the auxiliary radiation protection portion 44 but with the orientation being switched between left and right. Respective shapes and end portion shapes of an upper portion 46B, a lower portion 46C, a left side (outer side) portion 46D and a right side (inner side) side portion 46E of the protection portion main body 46A are similar to the shapes of the corresponding portions of the protection portion main body 44A.

In the first exemplary embodiment, the protection portion main bodies 44A and 46A are both formed of the same material as the material of the protection portion main body 42A of the main radiation protection portion 42. A surface treatment the same as the surface treatment applied to the main radiation protection portion 42 is applied to respective portions of the protection portion main bodies 44A and 46A against which the face of the test subject abuts.

As shown in FIG. 5 to FIG. 9, in the first exemplary embodiment, a reinforcing member 80 is provided substantially at an upper side half of the protection portion main body 44A of the auxiliary radiation protection portion. The reinforcing member 80 is superposed with the rear face side of the protection portion main body 44A and reinforces the protection portion main body 44A. The reinforcing member 80 is formed in a plate shape with an outline shape similar to the upper side half of the protection portion main body 44A. The reinforcing member 80 is disposed at least at a joining location with a first turning shaft 56 of a turning mechanism 54, which is described below, and at a disposition location of a second turning shaft 62 of a stowing mechanism 60, which is described below. A plate thickness of an upper portion 80E of the reinforcing member 80, which corresponds with the upper portion 44B of the protection portion main body 44A, is set to a thickness that both assures mechanical strength of the turning mechanism 54 and accommodates the second turning shaft 62 of the stowing mechanism 60. Accordingly, the plate thickness of the upper portion 80E is thicker than a plate thickness of a lower portion 80D at other portions of the reinforcing member 80, being, for example, three to five times thicker. The reinforcing member 80 is fixed to the protection portion main body 44A by fastening members 80A such as male screws or the like. As an example, an aluminum member, an aluminum alloy member or the like may be used as the reinforcing member 80, being higher in mechanical strength than the protection portion main body 44A, easy to machine mechanically, excellent in lightness of weight, and excellent in corrosion resistance. To aid understanding of the structure, the auxiliary radiation protection portion 46 is not shown in FIG. 5 to FIG. 9. However, similarly to the protection portion main body 44A, the reinforcing member 80 is also provided at the auxiliary radiation protection portion 46.

—Mounting Mechanism of the Radiography Protection Unit—

Figure 4:
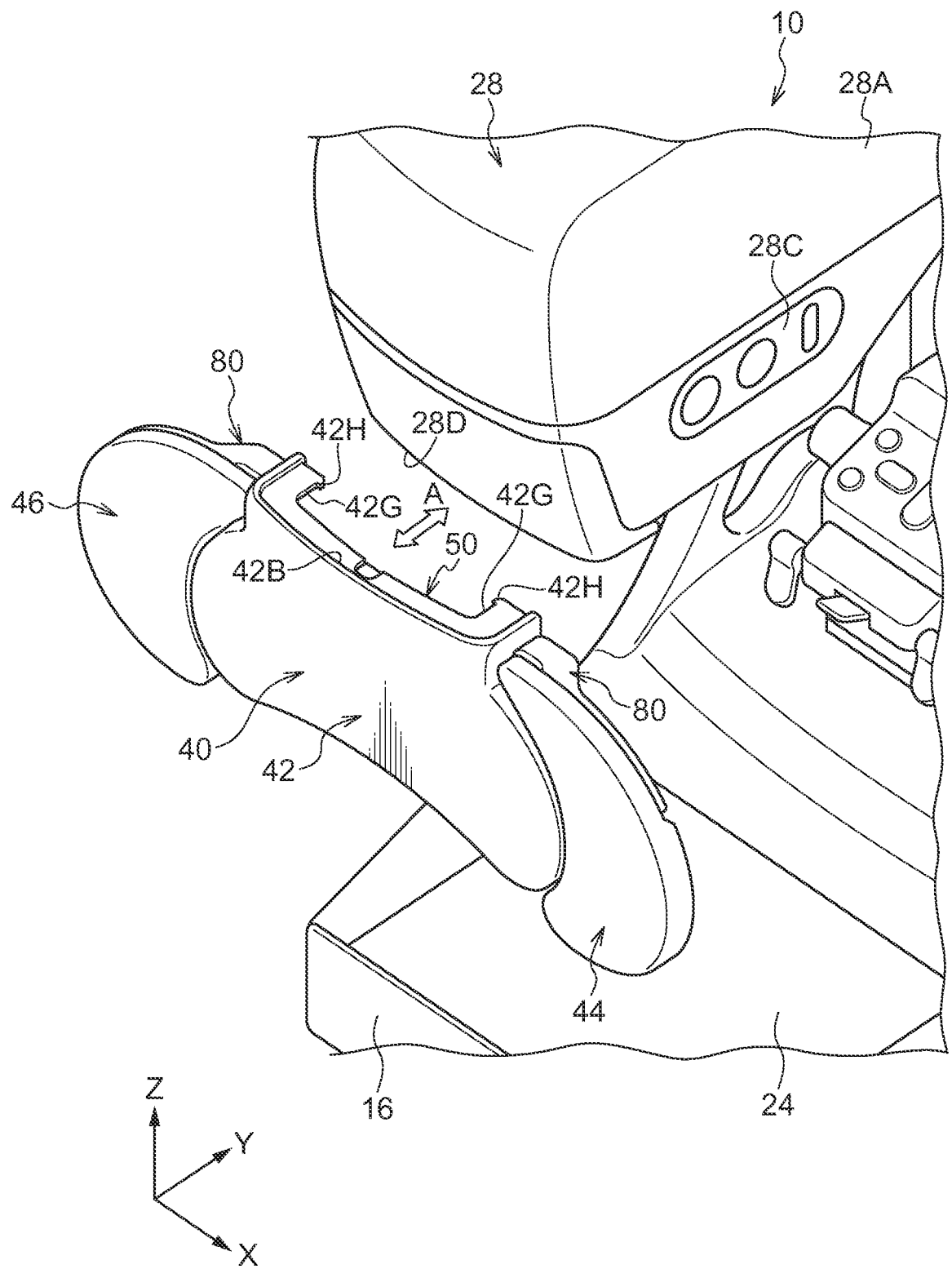
FIG. 4 is a perspective view showing the state of mounting of the radiography protection unit corresponding to FIG. 3, viewed from rightward and upward at the test subject side.

As shown in FIG. 3 and FIG. 4, the radiography protection unit 40 is detachably mounted at the radiation irradiation section 28 by a mounting mechanism that includes a mounting portion 52 provided at the floor face 28D of the radiation irradiation section 28 and a mounted portion 50 provided at the radiography protection unit 40. As shown in FIG. 3, the mounting portion 52 at the radiation irradiation section 28 is provided with a guide groove 28G and engaging portions 28H. The guide groove 28G is formed by a recessed groove that extends to left and right as viewed from the test subject side, then extends toward the rear face side at both the left and right sides, opening to the outer periphery side thereof. The engaging portions 28H are provided at end portions of the guide groove 28G at the rear face side, and are formed by hollows or incisions formed in floor portions of the guide groove 28G. The mounting portion 52 is fabricated of resin, the same as the casing 28A of the radiation irradiation section 28, and is integrally mounted at the casing 28A. Alternatively, the mounting portion 52 is fabricated as a separate component from the casing 28A and mounted thereto by fastening members such as screws, nuts and bolts, or the like. The mounting portion 52 may also be fabricated of, for example, a metallic member with excellent durability.

Correspondingly, as shown in FIG. 3 to FIG. 9, the mounted portion 50 at the radiography protection unit 40 is provided with a guided portion 42G and engaged portions 42H disposed at the upper portion 42B of the main radiation protection portion 42. The guided portion 42G is formed of a plate member in a "U" shape that opens to the rear face side in plan view. The guided portion 42G is structured to be fitted into the guide groove 28G of the mounting portion 52 by a movement of the radiography protection unit 40 from the test subject side toward the rear face side, the direction of arrow A in FIG. 3 and FIG. 4. The engaged portions 42H are formed in pawl shapes that protrude to the inner sides in plan view. The engaged portions 42H are engaged with the engaging portions 28H when most of the guided portion 42G has been fitted into the guide groove 28G. When the engaging portions 28H and the engaged portions 42H have engaged, the state in which the radiography protection unit 40 is mounted at the radiation irradiation section 28 is retained. If the engagement of the engaging portions 28H with the engaged portions 42H is released and then the radiography protection unit 40 is moved in the direction of arrow A away from the rear face side toward the test subject side, the guided portion 42G moves along the guide groove 28G and the radiography protection unit 40 is disengaged from the radiation irradiation section 28. The mounted portion 50 is formed integrally with the upper portion 42B of the main radiation protection portion 42.

—Moving Mechanism of the Radiography Protection Unit—

The radiography protection unit 40 is provided with a moving mechanism capable of moving each of the auxiliary radiation protection portion 44 and the auxiliary radiation protection portion 46 between a protecting position that protects the test subject against radiation and a non-protecting position that is withdrawn from the protecting position. To describe this further, the protecting position is at the test subject side of the region between the radiation irradiation section 28 and the imaging surface 24, in a region covering at least the face of the test subject in the state in which a radiographic image of a breast is being imaged. The protecting position may encompass regions above the breast that is the imaging target of the radiographic image, covering the shoulders, head and the like of the test subject. The protecting position may include a region that is separated from the test subject or a region that touches the test subject. The non-protecting position is a region at the rearward side of the main radiation protection portion 42, opposite the side thereof at which the test subject is disposed, so as not to be an obstacle to the test subject or to imaging of a radiographic image. The non-protecting positions are withdrawn positions at which the auxiliary radiation protection portions 44 and 46 are retracted from the protecting positions thereof.

As shown in FIG. 5 to FIG. 9, the moving mechanism is provided with the turning mechanism 54 and a retention and release mechanism 70. The turning mechanism 54 moves the auxiliary radiation protection portions 44 and 46 to turn between the protecting positions and the non-protecting positions. The retention and release mechanism 70 is capable of retaining the auxiliary radiation protection portions 44 and 46 at the main radiation protection portion 42 when they are at the protecting positions, and is capable of releasing this retention. The turning mechanism 54 includes the first turning shaft 56 and a first resilient member 58. The first turning shaft 56 includes shaft end portions 56A that protrude from each of two side portions of the main radiation protection portion 42 and are joined to each of the auxiliary radiation protection portions 44 and 46. The first turning shaft 56 is turnably disposed at the upper portion 42B of the protection portion main body 42A, with the axial direction thereof in a direction along an upper edge of the main radiation protection portion 42 (the X direction). The first turning shaft 56 is formed by, for example, a single rolled-steel member. An interlocking system that moves the auxiliary radiation protection portion 46 to match movements of the auxiliary radiation protection portion 44 is employed. The first turning shaft 56 may link two turning shafts: a turning shaft of the auxiliary radiation protection portion 44 and a turning shaft of the auxiliary radiation protection portion 46. The first resilient member 58 is, as an example in this case, a torsion coil spring. One end of the first resilient member 58 is fixed to the protection portion main body 42A and the other end of the first resilient member 58 is fixed to the first turning shaft 56. The first resilient member 58 provides a turning force to the first turning shaft 56 to cause the auxiliary radiation protection portions 44 and 46 to respectively turn from the protecting positions to the non-protecting positions.

As shown in FIG. 5 to FIG. 9, the retention and release mechanism 70 includes an operation portion 72, a linking portion 74A, a linking portion 74B, a retention and release portion 76, and a retained portion 44G. The operation portion 72 is disposed at a central portion of the protection portion main body 42A of the main radiation protection portion 42. The operation portion 72 is provided with a turning plate 72A that turns in the direction of arrow B in FIG. 5, about a turning shaft 72B whose axial direction is in the Y direction. The shape of the turning plate 72A is not particularly limited, but is a circular plate shape as viewed from the rear face side of the main radiation protection portion 42. The turning plate 72A is provided with an operation lever 72C that protrudes to the lower side from a lower periphery edge portion of the turning plate 72A.

Figure 5:
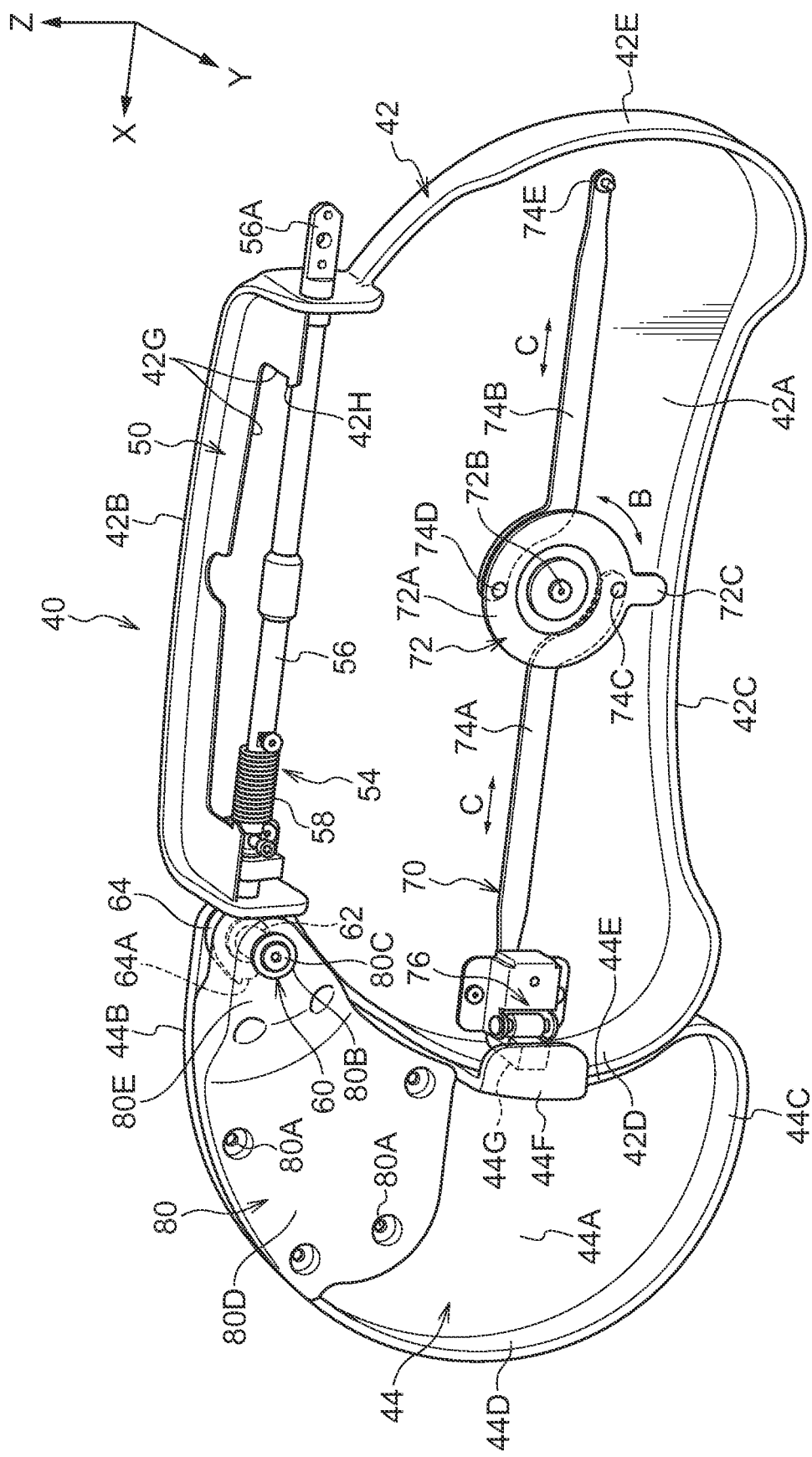
FIG. 5 is a perspective view of the radiography protection unit shown in FIG. 2 to FIG. 4, viewed from a rear face side that is opposite to the test subject side.

The linking portion 74A extends in the X direction from the operation portion 72 to the retention and release portion 76, which is disposed at the side portion 42D that is at the side of the protection portion main body 42A at which the auxiliary radiation protection portion 44 is disposed. One end of the linking portion 74A is turnably attached, via a pin 74C, to a portion of the turning plate 72A that is close to the operation lever 72C. An other end 74E of the linking portion 74A shown in FIG. 5 is linked to the retention and release portion 76, although detailed joining structure is not shown in the drawings. Similarly to the linking portion 74A, the linking portion 74B extends in the X direction from the operation portion 72 to another of the retention and release portion 76, which is not shown in the drawings, disposed at the side portion 42E at the side of the protection portion main body 42A at which the auxiliary radiation protection portion 46 is disposed. One end of the linking portion 74B is turnably attached, via a pin 74D, to a portion of the turning plate 72A that is a half-turn away from the operation lever 72C. The other end 74E of the linking portion 74B is linked to the retention and release portion 76 that is not shown in the drawings.

Figure 6:
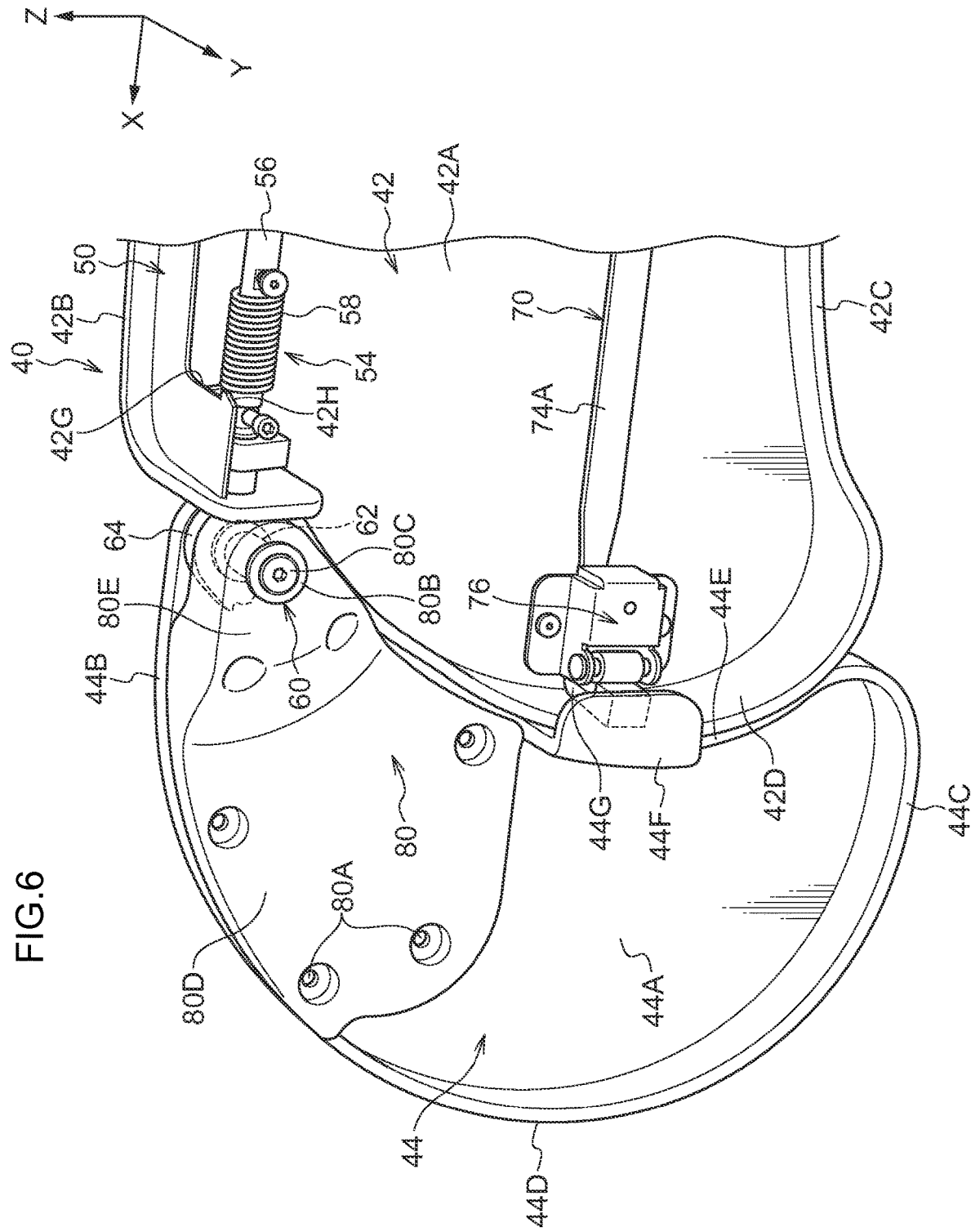
FIG. 6 is a magnified perspective view of principal portions of the radiography protection unit shown in FIG. 5.
Figure 7:
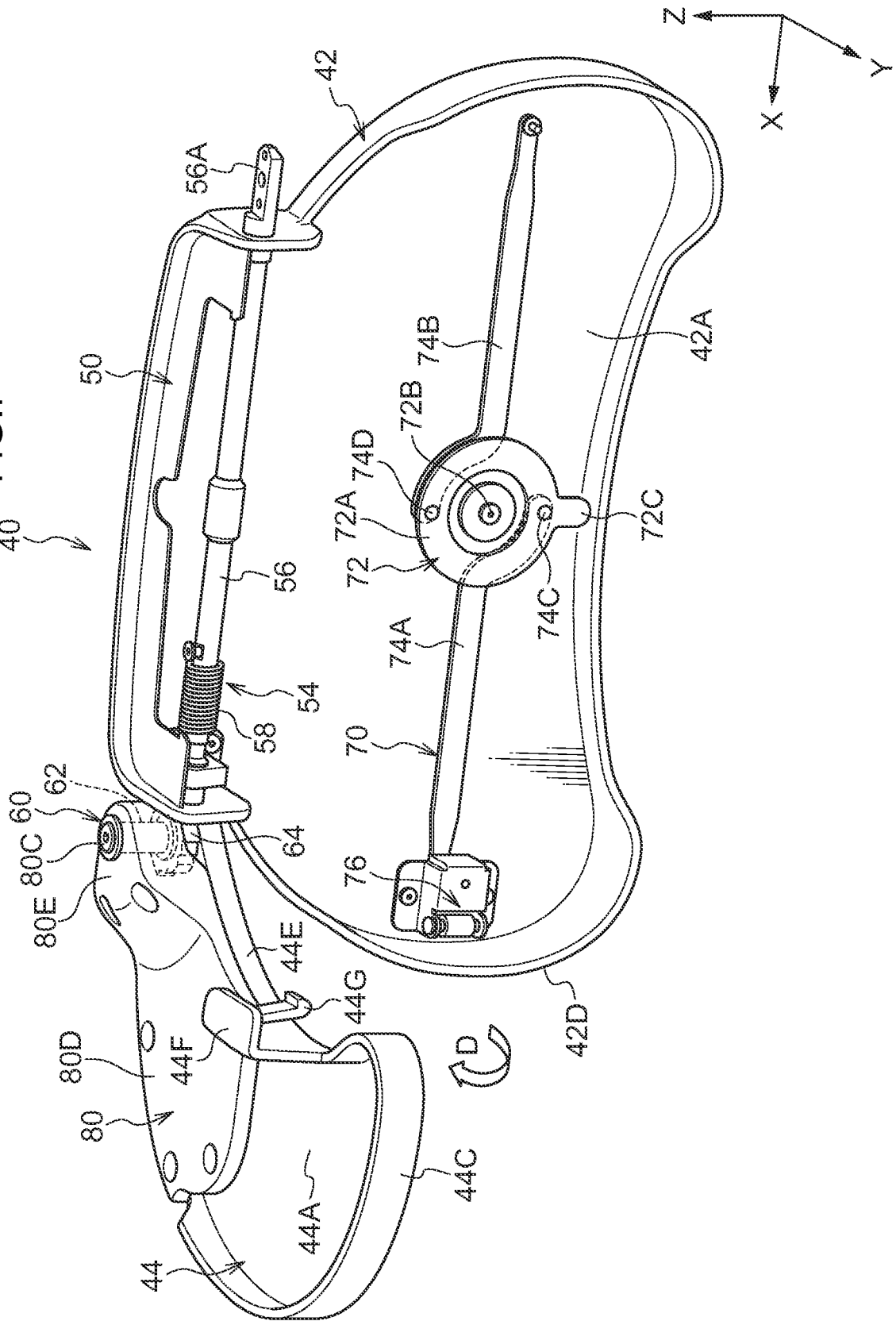
FIG. 7 is a perspective view, corresponding to FIG. 5, of the radiography protection unit when an auxiliary radiation protection portion is at a non-protecting position.

As shown in FIG. 5 to FIG. 7, particularly FIG. 7, the retained portion 44G is provided at a support portion 44F in an "L" shape, which protrudes to the rearward side from the side portion 44E of the protection portion main body 44A of the auxiliary radiation protection portion 44. The retained portion 44G is formed in a "J" shape, which is provided standing from the support portion 44F toward the front face side with the standing direction distal end protruding to the main radiation protection portion 42 side thereof. In the first exemplary embodiment, the support portion 44F and the retained portion 44G are formed integrally with the protection portion main body 44A, but this is not particularly limiting. Moreover, although not shown in the drawings, a retained portion similar to the retained portion 44G is integrally formed at the side portion 46E of the auxiliary radiation protection portion 46.

When the operation lever 72C of the retention and release mechanism 70 as shown in FIG. 5 is turned in the direction of arrow B, the linking portion 74A moves in the direction of arrow C and the retention of the retained portion 44G by the retention and release portion 76 is released. When the retention is released, the auxiliary radiation protection portion 44 that was retained at the protecting position is turned by the turning mechanism 54 in the direction of arrow D to the rearward side of the main radiation protection portion 42 and moves to the non-protecting position, as shown in FIG. 7. In this case, the auxiliary radiation protection portion 44 is turned by approximately 90° relative to the main radiation protection portion 42. In the first exemplary embodiment, movement of the auxiliary radiation protection portion 44 from the protecting position to the non-protecting position and movement of the auxiliary radiation protection portion 46 from the protecting position to the non-protecting position are interlocked. Conversely, movements from the non-protecting positions to the protecting positions are also interlocked.

Stowing Mechanism of the Radiography Protection Unit—

The radiography protection unit 40 is provided with the stowing mechanisms 60, each of which turns between the above-mentioned non-protecting position and a stowed position that is at the rear face side of the main radiation protection portion 42 relative to the non-protecting position. To describe this further, the stowed positions are in a region in which the auxiliary radiation protection portions 44 and 46 of the radiography protection unit 40 may be stowed to not be an obstacle at, for example, times when imaging is not being performed. The region at the rear face side of the main radiation protection portion 42 is a region that is irradiated with radiation during imaging, but is a free space when imaging is not being performed.

As shown in FIG. 5 to FIG. 9, each stowing mechanism 60 is provided with the second turning shaft 62, which turns the auxiliary radiation protection portion 44 or 46 between the non-protecting position and the stowed position, and a turning position retention mechanism, which retains respective turning positions of the auxiliary radiation protection portion 44 or 46 at the non-protecting position and the stowed position. One axial direction end of the second turning shaft 62 is turnably attached to the shaft end portion 56A of the first turning shaft 56 that protrudes to the upper portion 44B (the joining location) of the auxiliary radiation protection portion 44. Thus, the second turning shaft 62 is provided with the axial direction thereof in a direction intersecting the first turning shaft 56. In the first exemplary embodiment, the axial direction of the second turning shaft 62 is a direction orthogonal to the first turning shaft 56. The other axial direction end of the second turning shaft 62 is fixed by a fastening member 80C that is screwed into the second turning shaft 62 in the axial direction thereof, with a washer 80B interposed. The second turning shaft 62 is fixed to the reinforcing member 80 and is fixed to the auxiliary radiation protection portion 44 by this fastening member 80C. Consequently, the auxiliary radiation protection portion 44 is a structure that turns in the direction of arrow E about the second turning shaft 62 from the non-protecting position shown in FIG. 7 to the stowed position shown in FIG. 9. Although not shown in the drawings, another of the second turning shaft 62 is similarly provided at the shaft end portion 56A of the first turning shaft 56 that protrudes to the upper portion 46B (the joining location) of the auxiliary radiation protection portion 46. The auxiliary radiation protection portion 46 is fixed to this second turning shaft 62. Consequently, the auxiliary radiation protection portion 46 is a structure that turns about this second turning shaft 62. In the first exemplary embodiment, the turning of the auxiliary radiation protection portion 44 about the second turning shaft 62 is independent from the turning of the auxiliary radiation protection portion 46 about the other second turning shaft 62; turning of the two is not interlocked.

As shown in FIG. 8, the turning position retention mechanism is provided with a positioned portion 64 and a positioning portion 68. The positioned portion 64 has the same center of turning as the second turning shaft 62. The positioned portion 64 is structured by a plate-shaped member that includes, at a periphery edge portion, a non-protecting position portion 64A that is recessed at the non-protecting position and a stowed position portion 64B that is recessed at the stowed position. The positioned portion 64 is fixed to the shaft end portion 56A of the first turning shaft 56 by a fastening member such as a screw or the like, which is not shown in the drawings. The non-protecting position portion 64A is provided at the side portion 44D side in the auxiliary radiation protection portion 44 and at the side portion 46D side in the auxiliary radiation protection portion 46, respectively (see FIG. 2). The stowed position portion 64B is disposed apart from the non-protecting position portion 64A, and is disposed at the side portion 44E side in the auxiliary radiation protection portion 44 and at the side portion 46E side in the auxiliary radiation protection portion 46, respectively (see FIG. 2). The positioned portion 64 is fabricated of, for example, a curable resin that is easy to mold, a metal member with excellent durability, or the like.

The positioning portion 68 is fixed to the protection portion main body 44A of the auxiliary radiation protection portion 44. Thus, the respective turning positions of the auxiliary radiation protection portions 44 and 46 can be retained by each non-protecting position portion 64A and stowed position portion 64B. The retention of the turning position by the positioning portion 68 can be released by, for example, a manual operation by an operator. In the first exemplary embodiment, as an example, a ball plunger is employed as the positioning portion 68.

—Operation of the Radiography Protection Unit—

Operations to enlarge and reduce the range of protection against radiation of the radiography protection unit 40 described above are as follows.

Figure 10C:
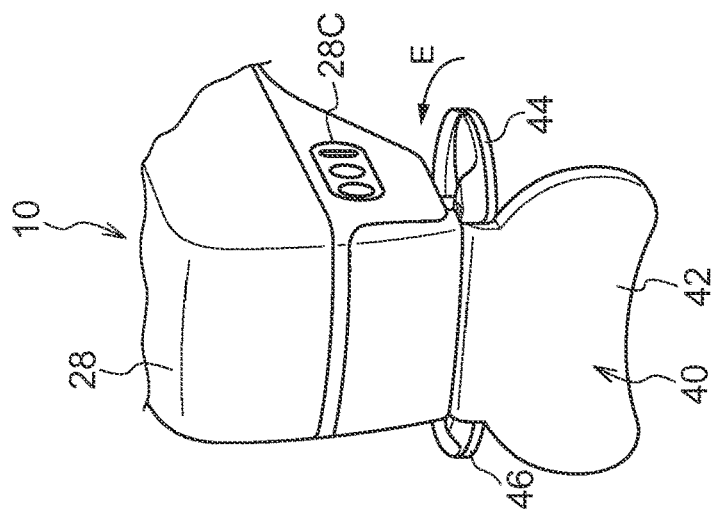
FIG. 10A, FIG. 10B and FIG. 10C are diagrams sequentially describing a procedure of changing a protection range of the radiography protection unit shown in FIG. 2 to FIG. 9.
Figure 10B:
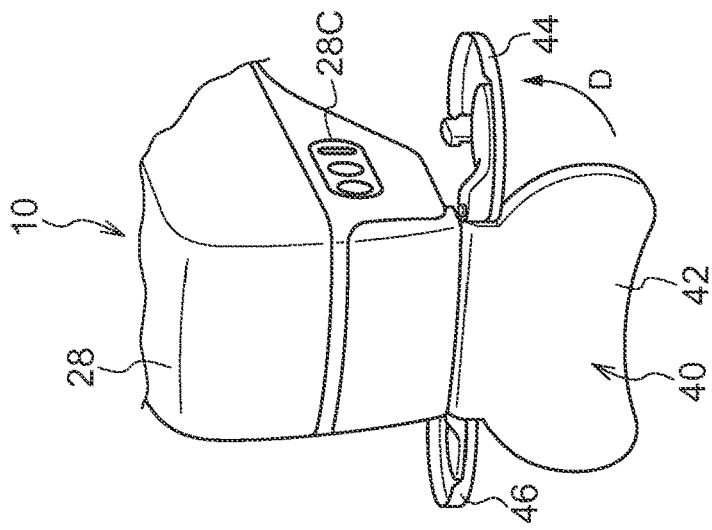
Figure 10A:
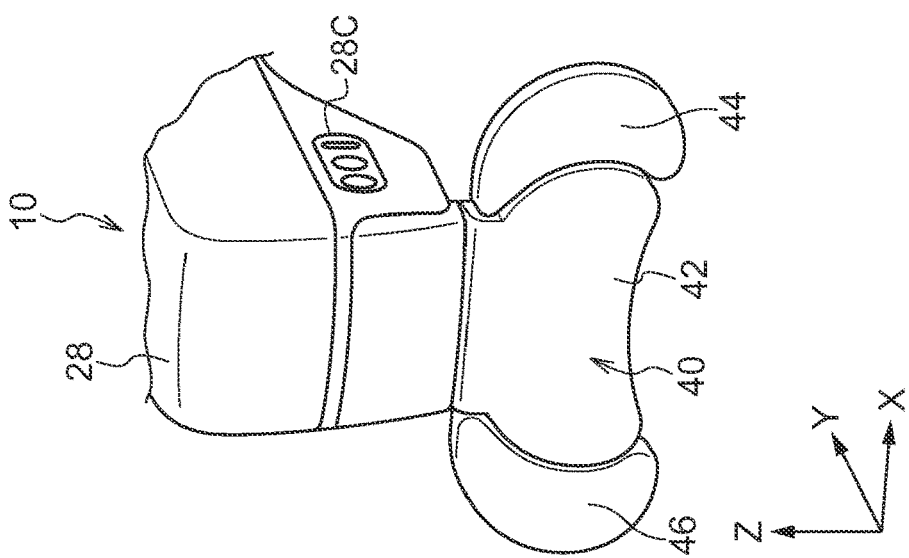

When a tomosynthesis image of the breast(s) of a test subject is to be imaged using the radiographic imaging device 10, as shown in FIG. 10A, the auxiliary radiation protection portions 44 and 46 of the radiography protection unit 40 are set to the protecting positions. At this time, the radiography protection unit 40 is in a state in which the retention and release portion 76 of each retention and release mechanism 70 retains the retained portion 44G. Thus, the auxiliary radiation protection portion 44 is retained at the side portion 42D of the main radiation protection portion 42 and the auxiliary radiation protection portion 46 is retained at the side portion 42E. Therefore, viewed from the test subject side, the range of protection against radiation is enlarged to left and right.

Figure 11:
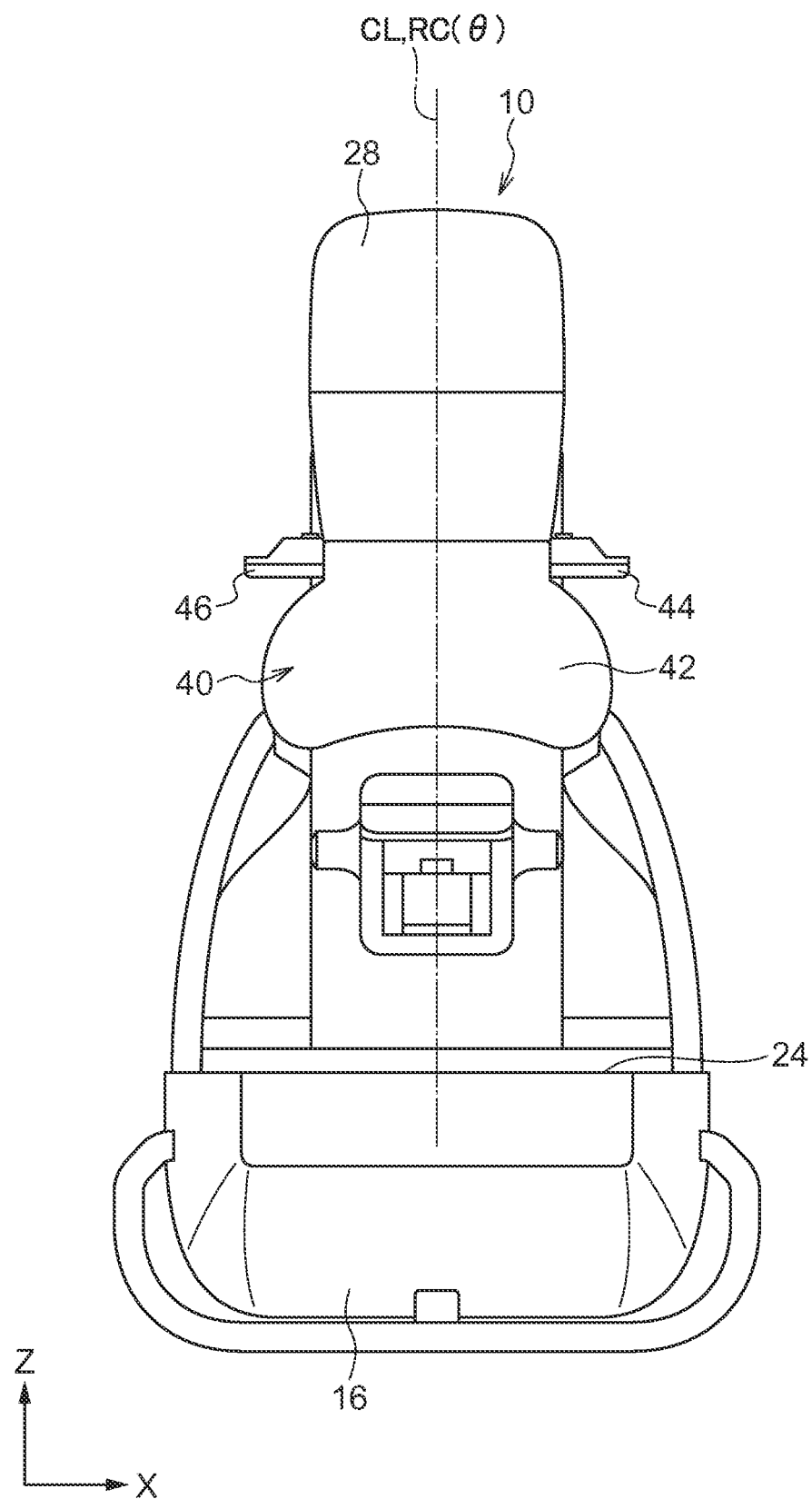
FIG. 11 is a front view of principal portions of the radiographic imaging device, viewed from the test subject side, showing a position of the radiation irradiation section and an inclination angle of an irradiation axis thereof during tomosynthesis imaging or during usual imaging.

In the radiographic imaging device 10 shown in FIG. 11, an irradiation angle of radiation from the radiation irradiation section 28 for usual imaging, with respect to a center line CL that is shown as appropriate, (the inclination angle of an irradiation axis RC of the radiation) is set to a perpendicular angle θ that matches the center line CL (for example, 0°). In the radiographic imaging device 10 shown in FIG. 12, the radiation irradiation section 28 is turned counterclockwise relative to the center line CL for tomosynthesis imaging, and an irradiation angle θ1 of the radiation is set to, for example, 10°. In the radiographic imaging device 10 shown in FIG. 13, the radiation irradiation section 28 is turned further counterclockwise relative to the center line CL for tomosynthesis imaging, and an irradiation angle θ2 of the radiation is set to, for example, 20°.

Figure 13:
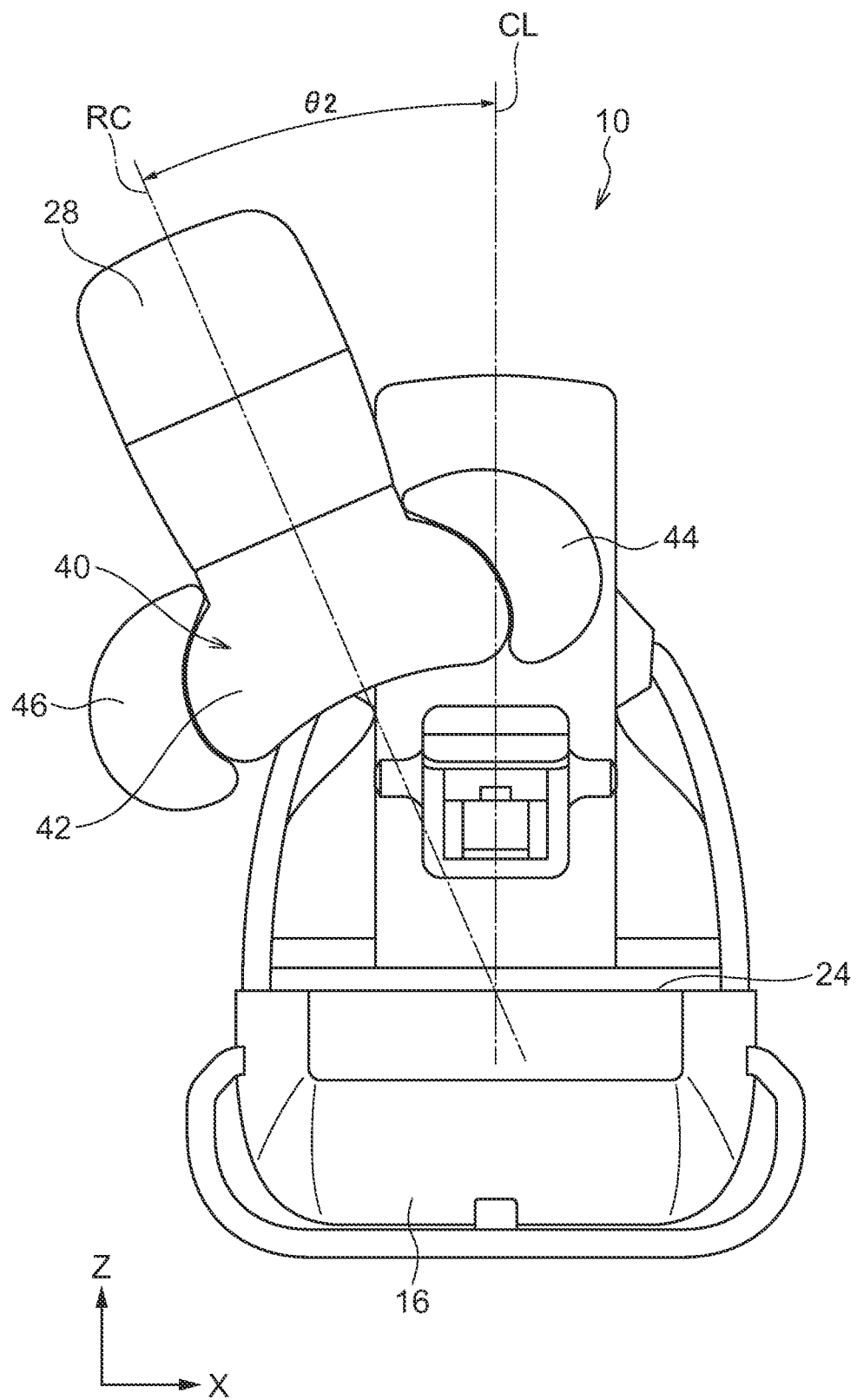
FIG. 13 is a front view of the principal portions of the radiographic imaging device, corresponding to FIG. 11, showing a position of the radiation irradiation section and an inclination angle of the irradiation axis (a deep inclination angle) during tomosynthesis imaging.

When the radiation is set to the irradiation angle θ2, the radiography protection unit 40 is turned counterclockwise to follow the counterclockwise turning of the radiation irradiation section 28 (see FIG. 13). Because the test subject is in, for example, an upright posture along the center line CL, depending on, for example, differences in heights of test subjects, the face area of the test subject may be disposed beyond the main radiation protection portion 42 of the radiography protection unit 40. In this case, because the auxiliary radiation protection portion 44 is in the protecting position, the range of protection against radiation is enlarged, and the face area is protected against the radiation by the auxiliary radiation protection portion 44.

Figure 12:
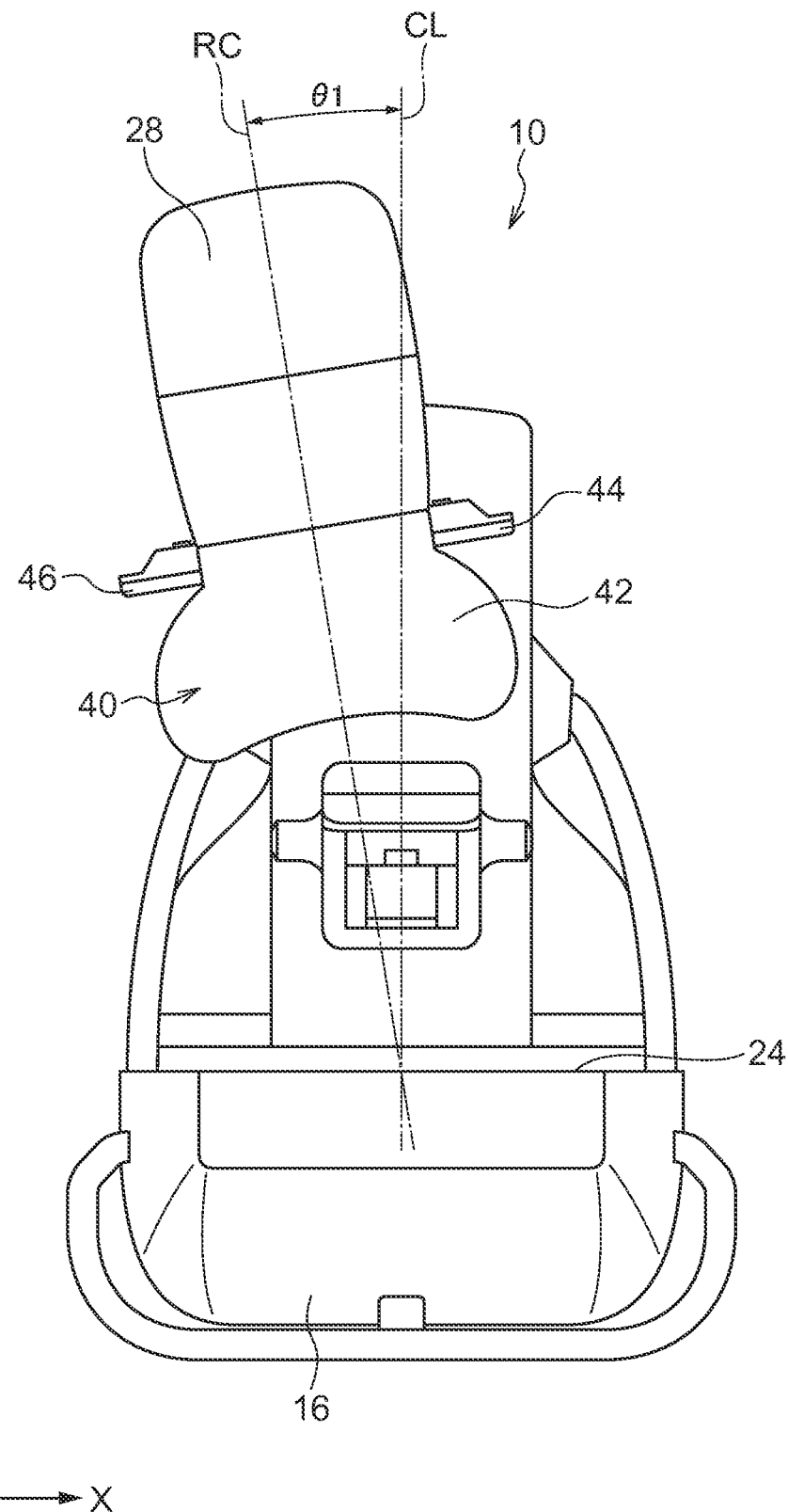
FIG. 12 is a front view of the principal portions of the radiographic imaging device, corresponding to FIG. 11, showing a position of the radiation irradiation section and an inclination angle of the irradiation axis (a shallow inclination angle) during tomosynthesis imaging.

When the usual imaging illustrated in FIG. 11 is being performed, or when tomosynthesis imaging is being performed at the shallow irradiation angle θ1 shown in FIG. 12, the auxiliary radiation protection portions 44 and 46 of the radiography protection unit 40 are set to the non-protecting positions as shown in FIG. 10B. The retention and release portion 76 of each retention and release mechanism 70 is in a state in which retention by the retained portion 44G is released, the auxiliary radiation protection portions 44 and 46 are retracted to the rearward sides from the side portion 42D or the side portion 42E of the main radiation protection portion 42 by the turning mechanism 54. The retraction of the auxiliary radiation protection portions 44 and 46 to their respective non-protecting positions is interlockingly and automatically implemented by an operation of the operation lever 72C. Consequently, as viewed from the test subject side, the range of protection against radiation is reduced to left and right, and protection against the radiation is implemented mainly by the main radiation protection portion 42.

When imaging is not being performed, as shown in FIG. 10C, the auxiliary radiation protection portions 44 and 46 of the radiography protection unit 40 are set to the stowed positions at the rear face side of the main radiation protection portion 42. At this time, at the turning position retention mechanism of each stowing mechanism 60, shown in FIG. 8, retention by the positioning portion 68 is moved from the non-protecting position portion 64A of the positioned portion 64 to the stowed position portion 64B. The respective movements of the auxiliary radiation protection portions 44 and 46 to the stowed positions are performed separately by manual operations by an operator.

Operation and Effects of the First Exemplary Embodiment

In the radiographic imaging device 10 according to the first exemplary embodiment, as shown in FIG. 1 and FIG. 2, the main radiation protection portion 42 and the auxiliary radiation protection portions 44 and 46 are provided. The main radiation protection portion 42 is disposed at the test subject side of the region between the imaging surface 24 of the imaging platform 16 and the radiation irradiation section 28. A test subject is protected from radiation by this main radiation protection portion 42. The auxiliary radiation protection portions 44 and 46 are disposed at the side portions 42D and 42E of the main radiation protection portion 42.

As shown in FIG. 5 to FIG. 7, FIG. 10A and FIG. 10B, the auxiliary radiation protection portions 44 and 46 are movable between the protecting positions and the non-protecting positions that are withdrawn from the protecting positions. Accordingly, when the auxiliary radiation protection portions 44 and 46 are at the protecting positions, a range in which radiation is shielded by the main radiation protection portion 42 and the auxiliary radiation protection portions 44 and 46 is widened. Thus, the range of protection from radiation is enlarged. On the other hand, when the auxiliary radiation protection portions 44 and 46 are withdrawn from the protecting positions to the non-protecting positions, the radiation is shielded only by the main radiation protection portion 42. Thus, the range of protection from radiation is reduced.

Therefore, according to the radiographic imaging device 10 in accordance with the first exemplary embodiment, suitable setting of a range of protection against radiation may be performed with ease.

Moreover, in the radiographic imaging device 10 according to the first exemplary embodiment, for example, as shown in FIG. 10A and FIG. 10B, the auxiliary radiation protection portions 44 and 46 are movable between the non-protecting positions at the rearward side of the main radiation protection portion 42 and the protecting positions. Hence, when the auxiliary radiation protection portions 44 and 46 have been withdrawn from the protecting positions to the non-protecting positions, the auxiliary radiation protection portions 44 and 46 can be stowed at the rearward side of the main radiation protection portion 42. Thus, stowing of the auxiliary radiation protection portions 44 and 46 when the range of protection against radiation is reduced can be excellently conducted.

In the radiographic imaging device 10 according to the first exemplary embodiment, as shown in FIG. 5 to FIG. 7, FIG. 10A and FIG. 10B, the auxiliary radiation protection portions 44 and 46 are structured to turn about the first turning shaft 56 provided at the side portions 42D and 42E of the main radiation protection portion 42. The axial direction of the first turning shaft 56 is in a direction along the upper edge of the main radiation protection portion 42, for example, the horizontal direction. Therefore, the auxiliary radiation protection portions 44 and 46 can be moved between the protecting positions and the non-protecting positions simply by being turned relative to the main radiation protection portion 42.

In the radiographic imaging device 10 according to the first exemplary embodiment, as shown in FIG. 8, FIG. 9, FIG. 10B and FIG. 10C, each of the auxiliary radiation protection portions 44 and 46 is structured to turn about the second turning shaft 62 of the stowing mechanism 60 that is provided at the first turning shaft 56 of the turning mechanism 54. Therefore, the auxiliary radiation protection portions 44 and 46 that have been moved from the protecting positions to the non-protecting positions can be further moved between the non-protecting positions and the stowed positions at the rear face side of the main radiation protection portion 42. Thus, stowing of the auxiliary radiation protection portions 44 and 46 when the range of protection against radiation is reduced may be excellently performed furthermore.

In the radiographic imaging device 10 according to the first exemplary embodiment, as shown in FIG. 5 to FIG. 7, the first resilient member 58 and the retention and release mechanism 70 are provided to serve as the moving mechanism. A turning force to turn the auxiliary radiation protection portions 44 and 46 from the protecting positions to the non-protecting positions is applied to the first turning shaft 56 by the first resilient member 58. The auxiliary radiation protection portions 44 and 46 at the protecting positions are retained by the retention and release mechanism 70 in opposition to the turning force from the first resilient member 58, at the side portions 42D and 42E of the main radiation protection portion 42, and this retention may be released by the retention and release mechanism 70. Consequently, when the retention of the retention and release mechanism 70 is released, the auxiliary radiation protection portions 44 and 46 are automatically turned from the protecting positions to the non-protecting positions by the turning force that is applied to the first turning shaft 56 by the first resilient member 58. Thus, an operation to change the range of protection against radiation from the enlarged range to the reduced range may be implemented by a simple operation by an operator.

In the radiographic imaging device 10 according to the first exemplary embodiment, as shown particularly in FIG. 8, the turning position retention mechanism of each stowing mechanism 60 is provided, and the turning positions of each of the auxiliary radiation protection portions 44 and 46 at each of the non-protecting position and the stowed position can be retained by the turning position retention mechanism. Specifically, each turning position retention mechanism is provided with the positioned portion 64, which includes the non-protecting position portion 64A and the stowed position portion 64B, and the positioning portion 68, which retains the turning position of the auxiliary radiation protection portion 44 or 46 at each of the non-protecting position portion 64A and the stowed position portion 64B. Therefore, the auxiliary radiation protection portions 44 and 46 may be immediately and reliably retained at their respective non-protecting positions and stowed positions. Thus, the operation of reducing the range of protection against radiation and the operation of stowing the auxiliary radiation protection portions 44 and 46 can be performed reliably.

In the radiographic imaging device 10 according to the first exemplary embodiment, as shown in FIG. 5 to FIG. 9, the auxiliary radiation protection portions 44 and 46 are provided with the protection portion main bodies 44A and 46A and each reinforcing member 80. The joining locations between the protection portion main bodies 44A and 46A and the first turning shaft 56 are reinforced by the reinforcing members 80. Further, the region of each of the protection portion main bodies 44A and 46A at which the stowing mechanism 60 is disposed is reinforced by the reinforcing member 80. Further yet, a region that is substantially half of the protection portion main body 44A or 46A at the upper portion 44B or 46B side thereof is reinforced by the reinforcing member 80. Thus, stiffness of the auxiliary radiation protection portions 44 and 46 may be improved.

In the radiographic imaging device 10 according to the first exemplary embodiment, as shown in, for example FIG. 1 and FIG. 2, the auxiliary radiation protection portions 44 and 46 are disposed at the side portions 42D and 42E at the two sides of the main radiation protection portion 42 of the radiography protection unit 40. Thus, the range of protection against radiation is further enlarged.

In the radiographic imaging device 10 according to the first exemplary embodiment, as shown particularly in FIG. 3 and FIG. 4, the main radiation protection portion 42 of the radiography protection unit 40 is detachably provided at the lower end portion (the floor face 28D in this case) of the radiation irradiation section 28. Therefore, the radiography protection unit 40 including the main radiation protection portion 42 as well as the auxiliary radiation protection portions 44 and 46 can be mounted and dismounted with ease. For example, the radiography protection unit 40 may be an optional part and may be easily assembled to the radiographic imaging device 10. Moreover, maintenance of the radiography protection unit 40 may be carried out easily. Because the radiography protection unit 40 is provided at the lower end portion of the radiation irradiation section 28, a mounting structure of the radiography protection unit 40 to the radiographic imaging device 10 can be simplified. For example, if the radiography protection unit 40 were assembled to the support section 22 shown in FIG. 1, support of the radiography protection unit 40 by a support arm extending from the support section 22 to the test subject side whilst avoiding the radiation irradiation region would be necessary. In this case, the assembly structure would be more complicated. Further, in the first exemplary embodiment, the radiography protection unit 40 is mounted to the radiation irradiation section 28, but the radiography protection unit 40 may be mounted to the test subject side of an upper portion of the compression plate 20.

In the radiographic imaging device 10 according to the first exemplary embodiment, as shown in, for example, FIG. 2, the side portions 42D and 42E of the main radiation protection portion 42 of the radiography protection unit 40 are both formed in curved shapes that protrude to the outer sides of the main radiation protection portion 42. Similarly, the side portion 44D and 46D at respective outer sides of the auxiliary radiation protection portions 44 and 46 are both formed in protruding curved shapes. Therefore, at a time of the usual imaging illustrated in FIG. 11 or at a time of the tomosynthesis imaging illustrated in FIG. 12, the overall left and right shapes of the radiography protection unit 40 are appeared, by the test subject, to be the curvilinear shapes of the side portions 42D and 42E of the main radiation protection portion 42. On the other hand, at a time of the tomosynthesis imaging illustrated in FIG. 13, the overall left and right shapes of the radiography protection unit 40 are appeared, by the test subject, to be the curvilinear shapes of the side portion 44D and 46D of the auxiliary radiation protection portions 44 and 46. Therefore, regardless of the imaging state, the radiography protection unit 40 appears gently curved from the test subject side, and the overall appearance (design) of the radiographic imaging device 10 may be improved compared to a rectangular shape. Furthermore, because the overall outline of the radiography protection unit 40 is gently curved, safety if the radiography protection unit 40 contacts with the test subject may be improved.

In the radiographic imaging device 10 according to the first exemplary embodiment, the side portions 42D and 42E of the main radiation protection portion 42 of the radiography protection unit 40 are both formed in curved shapes protruding to the outer sides of the main radiation protection portion 42. Moreover, the side portion 44D and side portion 46D at the outer sides of the auxiliary radiation protection portions 44 and 46 are both formed in protruding curved shapes, and the side portions 44E and 46E at the inner sides are both formed in curved shapes that are recessed so as to touch against the side portions 42D and 42E, respectively. Therefore, when the auxiliary radiation protection portions 44 and 46 are not at the non-protecting positions but at the stowed positions shown in FIG. 10C, the radiation generation source 28B is not blocked by these recessed portions. Thus, the usual imaging illustrated in FIG. 11 and the tomosynthesis imaging illustrated in FIG. 12 are possible.

The radiography protection unit 40 according to the first exemplary embodiment may be fabricated as a separate component such as an optional part as mentioned above. Therefore, because the radiography protection unit 40 may be easily mounted to a radiographic imaging device not equipped with the radiography protection unit 40, the radiographic imaging device 10 that may achieve the operations and effects of the first exemplary embodiment may be embodied with ease.

First Variant Example

The radiographic imaging device 10 and radiography protection unit 40 are described in accordance with a first variant example of the first exemplary embodiment, using FIG. 14. In the first variant example, excellent boundary locations between the main radiation protection portion 42 and the auxiliary radiation protection portions 44 and 46 of the radiography protection unit 40 are described.

As shown in FIG. 14, in the radiographic imaging device 10 according to the first variant example, a boundary location 40A between the main radiation protection portion 42 and the auxiliary radiation protection portion 44 of the radiography protection unit 40 is specified to be, as viewed from the test subject side, between an irradiation region R of the radiation and a side face at the right side of the radiation irradiation section 28. Meanwhile, a boundary location 40B between the main radiation protection portion 42 and the auxiliary radiation protection portion 46 is specified to be between the irradiation region R of the radiation and a side face at the left side of the radiation irradiation section 28 as viewed from the test subject side. Herein, the term "irradiation region R" is intended to include a conical region that widens from a central position of the radiation generation source 28B to an effective detection region ER of the radiation detection panel 30. Each of the boundary locations 40A and 40B is separated by a distance L1 from the irradiation region R, and each of the boundary locations 40A and 40B is separated by a distance L2 from a side portion of the radiation irradiation section 28. These distances L1 and L2 are tolerance dimensions.

In the radiographic imaging device 10 according to the first variant example, because the boundary locations 40A and 40B between the main radiation protection portion 42 and auxiliary radiation protection portions 44 and 46 of the radiography protection unit 40 are specified to be at out sides relative to the radiation irradiation region R, the range of protection against radiation may be assured. On the other hand, because the boundary locations 40A and 40B are specified to be at inner sides relative to the side faces of the radiation irradiation section 28, and the auxiliary radiation protection portions 44 and 46 are stowed towards the irradiation region R, a space for stowing the auxiliary radiation protection portions 44 and 46 at the non-protecting positions can be saved. With the radiography protection unit 40 according to the first variant example, the radiographic imaging device 10 that may achieve these operations and effects may be embodied.

In the radiographic imaging device and radiography protection unit according to each of a second variant example, a third variant example, a second exemplary embodiment, and a variant example of the second exemplary embodiment described below, excellent boundary locations may be specified in the same manner as in this first variant example.

Second Variant Example

Figure 15:
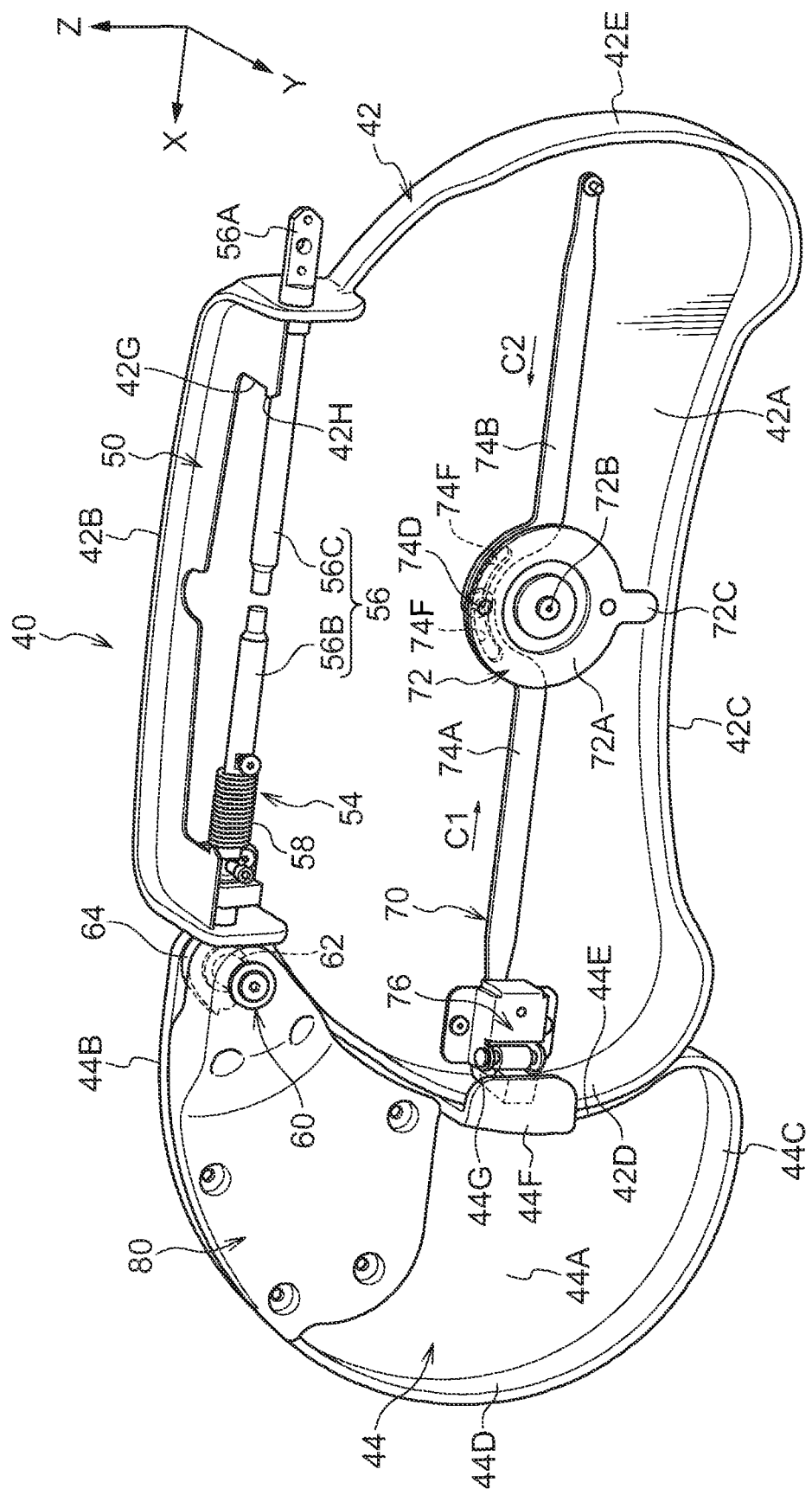
FIG. 15 is a perspective view of principal portions of a radiography protection unit that is provided at a radiographic imaging device in accordance with a second variant example of the first exemplary embodiment, viewed from a rear face side.

The radiographic imaging device and radiography protection unit are described in accordance with a second variant example of the first exemplary embodiment, using FIG. 15. In the second variant example, the turning mechanism and the retention and release mechanism of the radiography protection unit is changed. An example is described in which the auxiliary radiation protection portions disposed at the two side portions of the main radiation protection portion are not interlocked but respectively separately operated.

As shown in FIG. 15, in the radiographic imaging device 10 according to the second variant example, the first turning shaft 56 of the turning mechanism 54 of the radiography protection unit 40 is divided, in the axial direction, into a first turning shaft 56B and a second turning shaft 56C. The shaft end portion 56A of the first turning shaft 56B protrudes from the side portion 42D side of the main radiation protection portion 42 and is joined to the auxiliary radiation protection portion 44 via the stowing mechanism 60. Meanwhile, although not shown in the drawing, the shaft end portion 56A of the second turning shaft 56C protrudes from the side portion 42E side of the main radiation protection portion 42 and is similarly joined to the auxiliary radiation protection portion 46 via the stowing mechanism 60 (see FIG. 2). That is, the first turning shaft 56B and the second turning shaft 56C turn respectively independently. Other structures of the turning mechanism 54, such as the first resilient member 58 and the like, are substantially the same as the structures of the turning mechanism 54 according to the first exemplary embodiment.

In this retention and release mechanism 70, the pin 74D is provided at the turning plate 72A at a location that is opposite from the operation lever 72C of the operation portion 72. A circular arc-shaped long hole 74F, which is formed at one end of the linking portion 74A, and a circular arc-shaped long hole 74F, which is formed at one end of the linking portion 74B, engage with the pin 74D. When the turning plate 72A is turned clockwise in FIG. 15 by the operation lever 72C, the linking portion 74A moves in the direction of arrow C1 and the retention of the retained portion 44G by the retention and release portion 76 is released. As a result, the auxiliary radiation protection portion 44 automatically moves from the protecting position to the non-protecting position. On the other hand, when the turning plate 72A is turned counterclockwise by the operation lever 72C, the linking portion 74B moves in the direction of arrow C2 and, similarly, the auxiliary radiation protection portion 46 automatically moves from the protecting position to the non-protecting position.

In the radiographic imaging device 10 according to the second variant example, the auxiliary radiation protection portions 44 and 46 of the radiography protection unit 40 are respectively separately movable. Therefore, the range of protection against radiation may be made switchable in stages. To describe this more specifically, the range of protection is switchable between the enlarged range of protection that is specified when both of the auxiliary radiation protection portions 44 and 46 are at the protecting positions, an intermediate range of protection that is specified when one of the auxiliary radiation protection portions 44 and 46 is at the protecting position and the other is at the non-protecting position, and the reduced range of protection that is specified when both of the auxiliary radiation protection portions 44 and 46 are at the non-protecting positions. With the radiography protection unit 40 according to the second variant example, the radiographic imaging device 10 that may achieve these operations and effect may be embodied.

Third Variant Example

Figure 16:
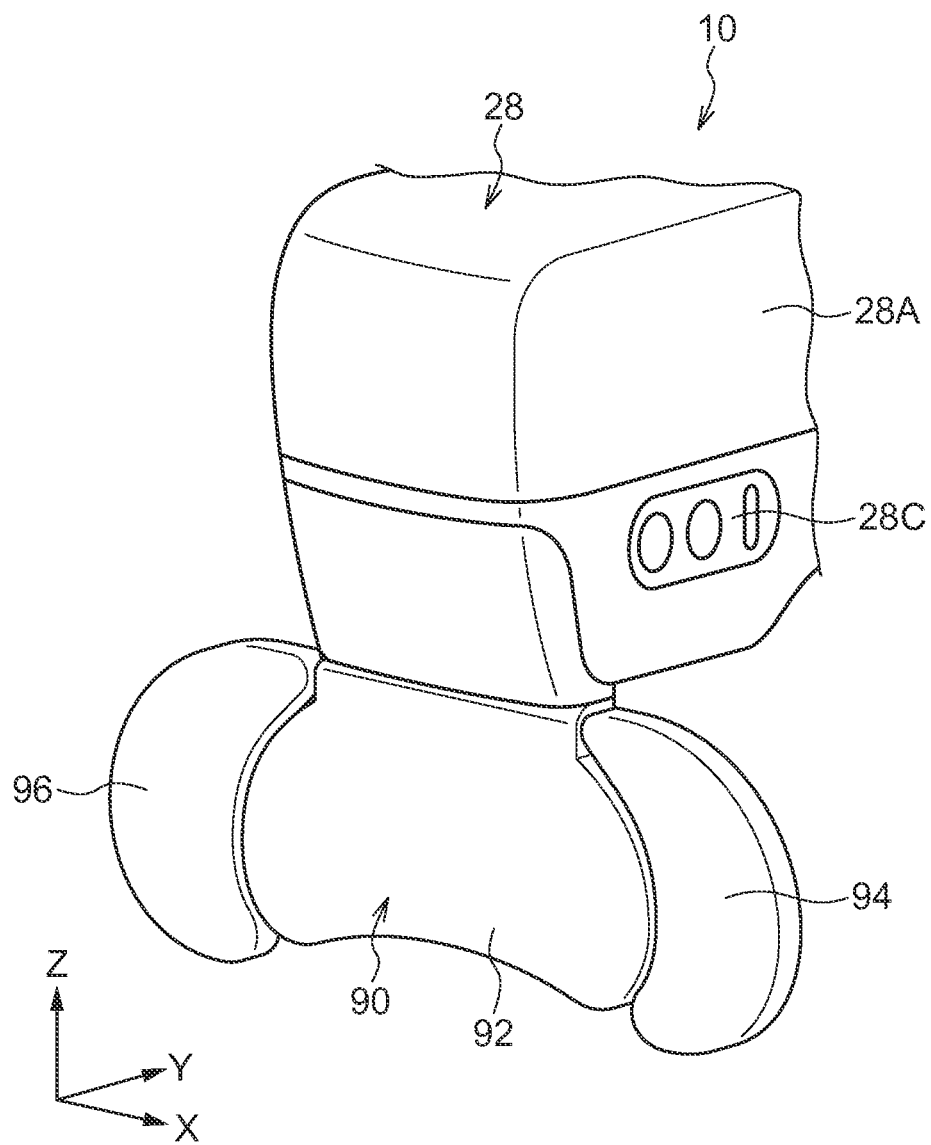
FIG. 16 is a perspective view, corresponding to FIG. 10A, of principal portions of a radiographic imaging device in accordance with a third variant example of the first exemplary embodiment, when the auxiliary radiation protection portions are at the protecting positions.
Figure 17:
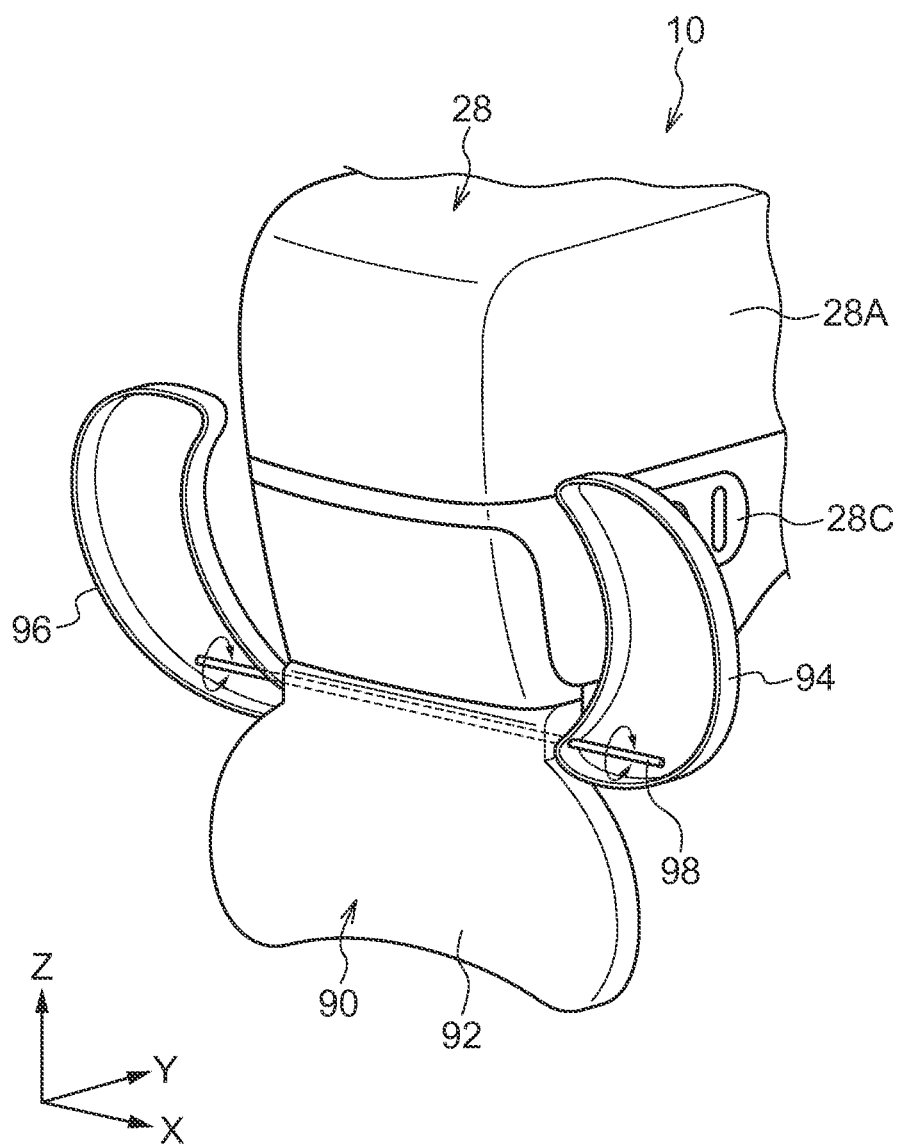
FIG. 17 is a perspective view, corresponding to FIG. 10B, of the principal portions of the radiographic imaging device in accordance with the third variant example, when the auxiliary radiation protection portions are at the non-protecting positions.
Figure 18:
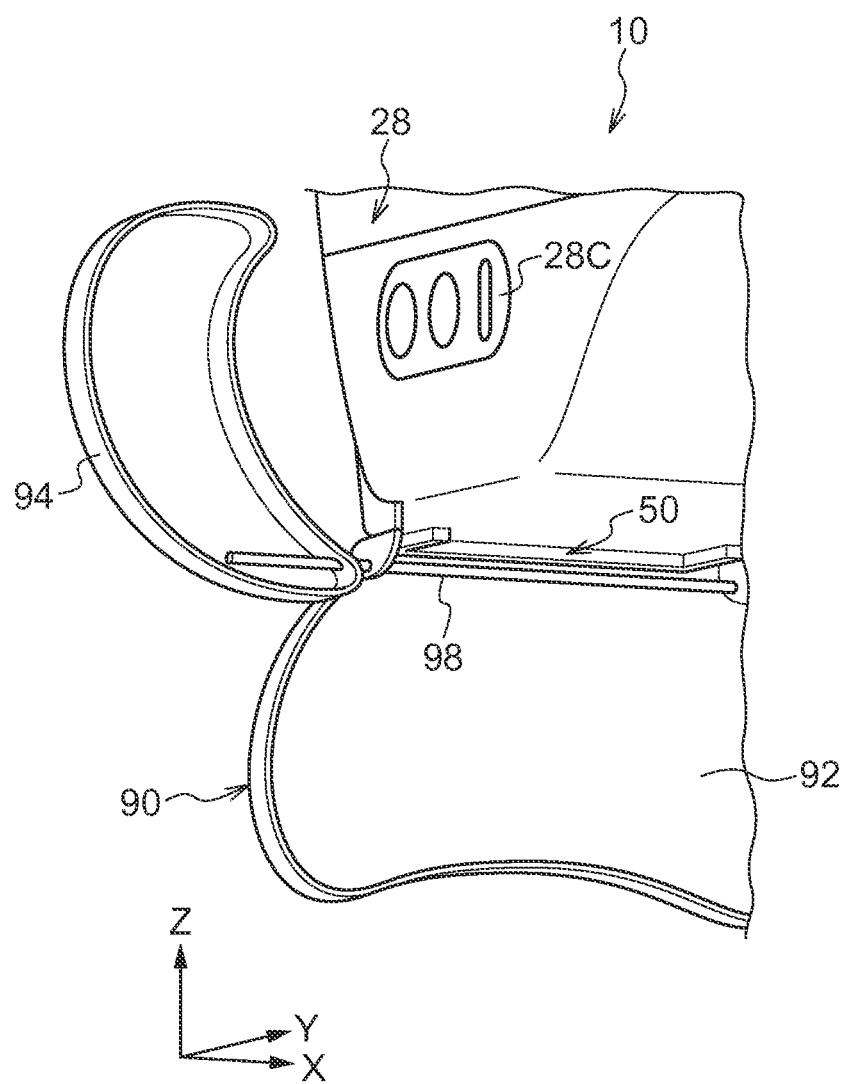
FIG. 18 is a perspective view of principal portions of the radiography protection unit shown in FIG. 17, viewed from rearward of the right side at the rear face side.

The radiographic imaging device and radiography protection unit are described in accordance with a third variant example of the first exemplary embodiment, using FIG. 16 to FIG. 18. In the third variant example, the turning mechanism of the radiography protection unit is changed such that the structure of the turning mechanism of the auxiliary radiation protection portion is simplified.

As shown in FIG. 16, the radiographic imaging device 10 according to the third variant example is provided with a radiography protection unit 90 similar to the radiography protection unit 40 according to the first exemplary embodiment. The radiography protection unit 90 is provided with a main radiation protection portion 92, which is detachably mounted at the radiation irradiation section 28, and auxiliary radiation protection portions 94 and 96, which are disposed at the two left and right side portions of the main radiation protection portion 92. The auxiliary radiation protection portions 94 and 96 shown in FIG. 16 are both set to the protecting positions.

As shown in FIG. 17 and FIG. 18, a first turning shaft 98 is provided in the radiography protection unit 90. The axial direction of the first turning shaft 98 is set to a direction along the upper edge of the main radiation protection portion 92 (the X direction) at the side portions of the main radiation protection portion 92. The auxiliary radiation protection portions 94 and 96 are both joined to the first turning shaft 98, and are structured to turn about the first turning shaft 98 between the protecting positions and the non-protecting positions. The auxiliary radiation protection portions 94 and 96 shown in FIG. 17 are both set to the non-protecting positions, at the upper side of the main radiation protection portion 92. The non-protecting positions may be designated at the rearward side of the main radiation protection portion 92 similar to the non-protecting positions of the radiography protection unit 40 according to the first exemplary embodiment.

In the radiographic imaging device 10 according to the third variant example, the auxiliary radiation protection portions 94 and 96 turn about the first turning shaft 98 provided at the side portions of the main radiation protection portion 92. Therefore, the auxiliary radiation protection portions 94 and 96 can be moved between the protecting positions and the non-protecting positions simply by being turned relative to the main radiation protection portion 92. Thus, according to the radiographic imaging device 10 according to the third variant example, the range of protection against radiation may be enlarged and reduced with ease.

In the radiographic imaging device 10 according to the third variant example, compared to the turning mechanism 54 of the radiographic imaging device 10 according to the first exemplary embodiment, the auxiliary radiation protection portions 94 and 96 are made movable by a simple structure of the first turning shaft 98 alone. Therefore, the structure of the radiographic imaging device 10 may be simplified. Furthermore, in the radiographic imaging device 10 according to the third variant example, the stowing mechanism 60 of the radiographic imaging device 10 according to the first exemplary embodiment is not provided. Thus, simplification may be furthermore realized. With the radiography protection unit 90 according to the third variant example, the radiographic imaging device 10 that may achieve these operations and effects may be embodied.

Second Exemplary Embodiment

Figure 19:
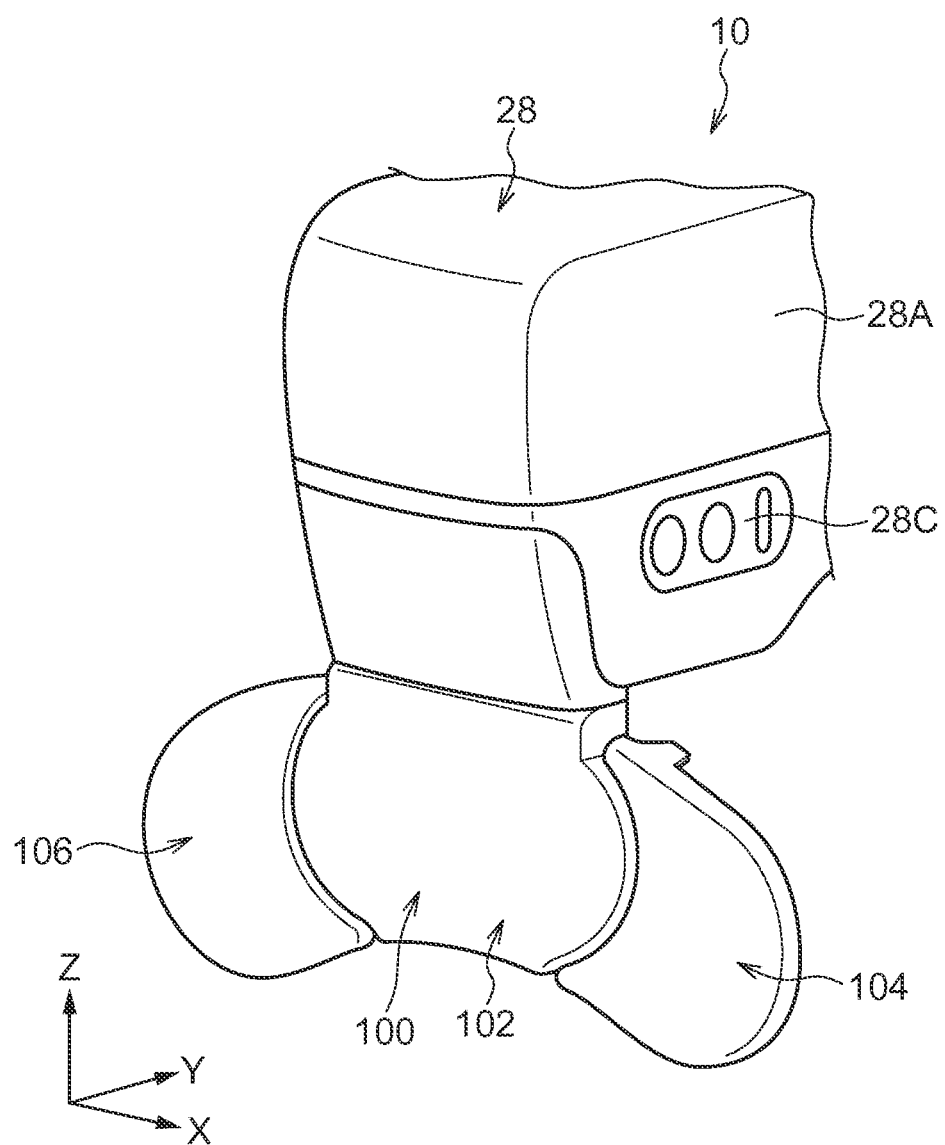
FIG. 19 is a perspective view, corresponding to FIG. 16, of the principal portions of a radiographic imaging device in accordance with a second exemplary embodiment of the present invention, when the auxiliary radiation protection portions are at the protecting positions.
Figure 20:
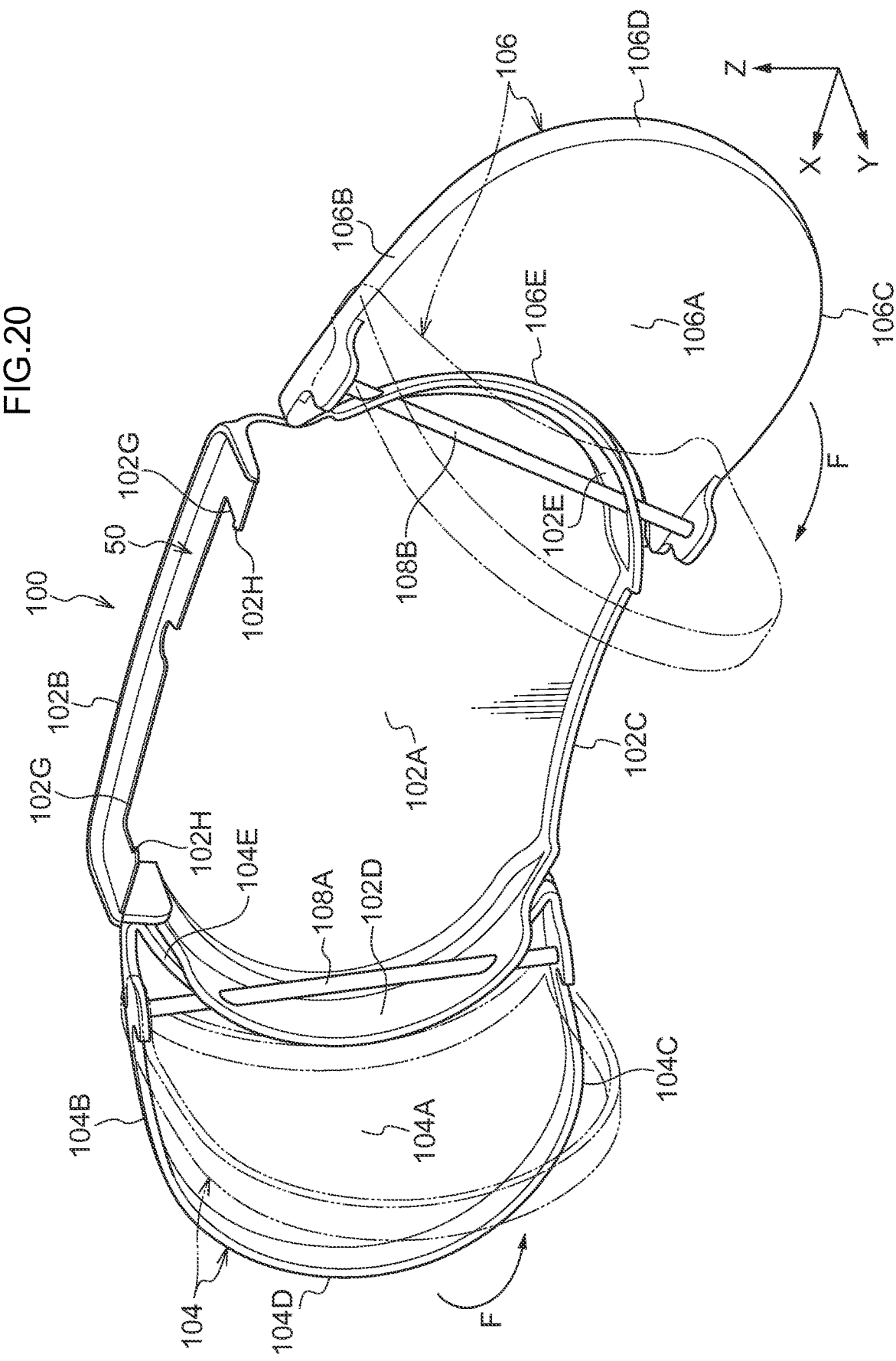
FIG. 20 is a magnified perspective view of the radiography protection unit shown in FIG. 19, viewed from the rear face side thereof.
Figure 21:
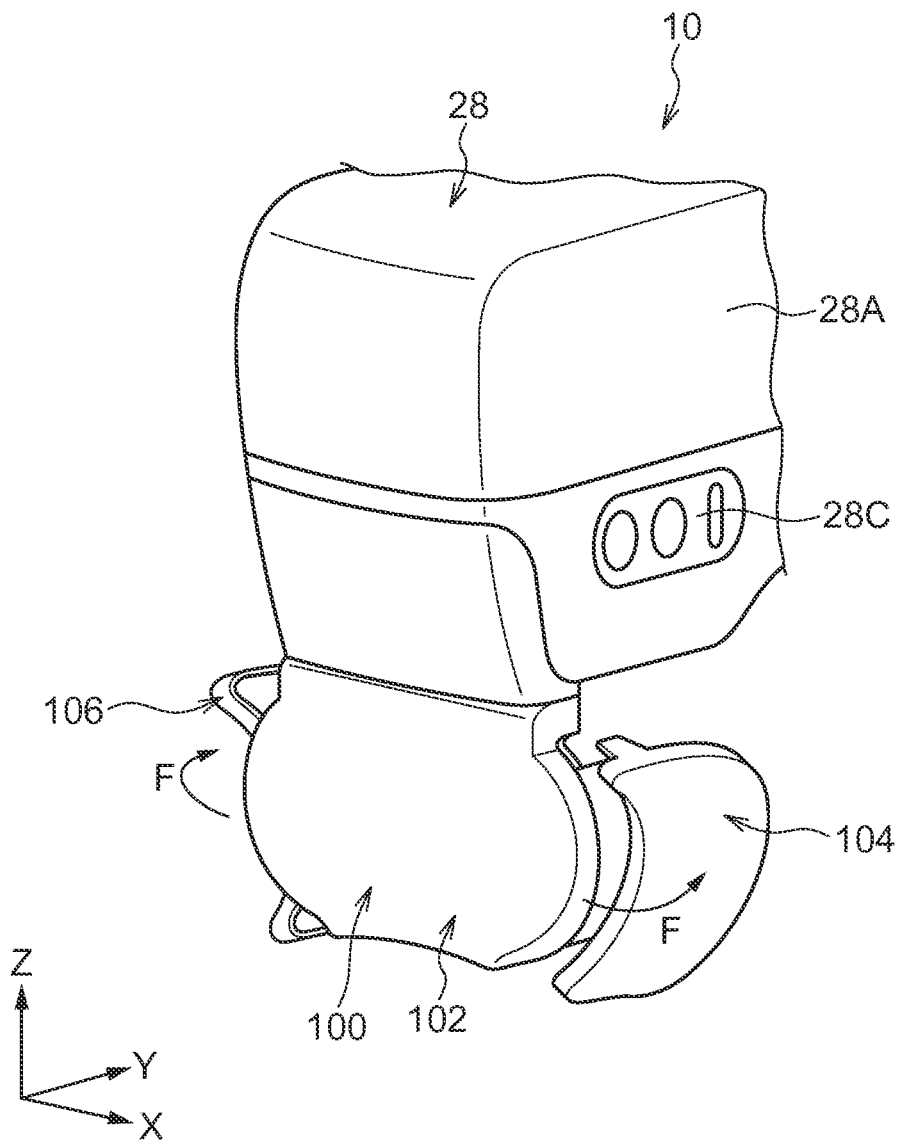
FIG. 21 is a perspective view, corresponding to FIG. 17, of the principal portions of the radiographic imaging device in accordance with the second exemplary embodiment, when the auxiliary radiation protection portions are at the non-protecting positions.

The radiographic imaging device and radiography protection unit are described in accordance with a second exemplary embodiment of the present invention, using FIG. 19 to FIG. 21. The second exemplary embodiment is a variant example of the turning mechanism of the radiography protection unit: an example in which the direction of movement of the auxiliary radiation protection portions is altered is described.

—Structure of the Radiography Protection Unit—

As shown in FIG. 19, the radiographic imaging device 10 according to the second exemplary embodiment is provided with a radiography protection unit 100 similar to the radiography protection unit 40 according to the first exemplary embodiment. The radiography protection unit 100 is provided with a main radiation protection portion 102, which is detachably mounted at the radiation irradiation section 28, and auxiliary radiation protection portions 104 and 106, which are disposed at the two left and right side portions of the main radiation protection portion 102. The auxiliary radiation protection portions 104 and 106 shown in FIG. 19 are both set to the protecting positions.

—Structure of the Main Radiation Protection Portion—

As shown in FIG. 20, similarly to the main radiation protection portion 42 of the first exemplary embodiment, the main radiation protection portion 102 of the radiography protection unit 100 is provided with a protection portion main body 102A that is formed by a plate member including an upper portion 102B, a lower portion 102C, and side portions 102D and 102E. An upper face of the upper portion 102B is formed in a flat shape in the horizontal direction, to match the shape of the floor face 28D of the radiation irradiation section 28 (see FIG. 3). The mounted portion 50 is disposed at the upper portion 102B, and the mounted portion 50 is provided with a guided portion 102G and engaged portions 102H. The lower portion 102C and the side portions 102D and 102E are formed in curved shapes similar to the lower portion 42C and the side portions 42D and 42E, respectively, of the radiography protection unit 40. The main radiation protection portion 102 is fabricated of the same material as the main radiation protection portion 42 of the radiography protection unit 40.

—Structure of the Auxiliary Radiation Protection Portion—

As shown in FIG. 20, similarly to the auxiliary radiation protection portion 44 of the first exemplary embodiment, the auxiliary radiation protection portion 104 is provided with a protection portion main body 104A that is formed of a plate member in a crescent moon shape. The protection portion main body 104A includes an upper portion 104B, a lower portion 104C, and side portions 104D and 104E. Similarly to the auxiliary radiation protection portion 46 of the first exemplary embodiment, the auxiliary radiation protection portion 106 is provided with a protection portion main body 106A that is formed of a plate member in a crescent moon shape, and the protection portion main body 106A includes an upper portion 106B, a lower portion 106C, and side portions 106D and 106E. The auxiliary radiation protection portions 104 and 106 are both fabricated of the same material as the auxiliary radiation protection portions 44 and 46 of the radiography protection unit 40.

—Moving Mechanism of the Radiography Protection Unit—

The radiographic imaging device 10 according to the second exemplary embodiment is equipped with a moving mechanism. This moving mechanism is provided with a third turning shafts 108A and 108B at the side portions 102D and 102E of the main radiation protection portion 102. The axial directions of the third turning shafts 108A and 108B are set to directions along the irradiation axis of the radiation. The term "the radiation axis of the irradiation" as used here is equivalent to the radiation axis RC of the radiation that is shown in FIG. 11 to FIG. 13.

The third turning shaft 108A is provided to pierce through a rib portion of the side portion 102D in the Z direction. One end of the third turning shaft 108A, at the upper side, is joined to the upper portion 104B of the auxiliary radiation protection portion 104, and the other end, at the lower side, is joined to the lower portion 104C. Thus, the auxiliary radiation protection portion 104 is structured to turn in the direction of arrow F about the third turning shaft 108A between the protecting position and the non-protecting position, as illustrated by the two-dot chain lines in FIG. 20 and the solid lines in FIG. 21. In other words, the auxiliary radiation protection portion 104 is a structure that folds from the protecting position, at the test subject side of the side portion 102D of the main radiation protection portion 102, to the non-protecting position that is disposed at the rearward side of the main radiation protection portion 102.

Similarly, the third turning shaft 108B is provided to pierce through a rib portion of the side portion 102E in the Z direction. One end of the third turning shaft 108B, at the upper side, is joined to the upper portion 106B of the auxiliary radiation protection portion 106, and the other end, at the lower side, is joined to the lower portion 106C. Thus, the auxiliary radiation protection portion 106 is structured to turn about the third turning shaft 108B between the protecting position and the non-protecting position, as illustrated in FIG. 20 and FIG. 21. Thus, the auxiliary radiation protection portion 106 is a structure that folds from the protecting position, at the test subject side of the side portion 102E of the main radiation protection portion 102, to the non-protecting position that is disposed at the rearward side of the main radiation protection portion 102. In the second exemplary embodiment, the auxiliary radiation protection portions 104 and 106 are not interlinked but respectively independently movable.

Operation and Effects of the Second Exemplary Embodiment

In the radiographic imaging device 10 according to the second exemplary embodiment, the auxiliary radiation protection portions 104 and 106 turn about the third turning shafts 108A and 108B provided at the side portions 102D and 102E of the main radiation protection portion 102. The axial directions of the third turning shafts 108A and 108B are in directions along the irradiation axis of the radiation, for example, substantially vertical directions. Therefore, the auxiliary radiation protection portions 104 and 106 can be moved between the protecting positions and the non-protecting positions simply by being turned relative to the main radiation protection portion 102. Thus, the range of protection against radiation may be enlarged and reduced with ease.

Further, in the radiographic imaging device 10 according to the second exemplary embodiment, the auxiliary radiation protection portions 104 and 106 may be moved between the protecting positions and the non-protecting positions. Therefore, the tomosynthesis imaging with a large irradiation angle illustrated in FIG. 13 may be performed when the auxiliary radiation protection portions 104 and 106 are at the protecting positions, and the usual imaging illustrated in FIG. 11 and the tomosynthesis imaging with a small irradiation angle illustrated in FIG. 12 may be performed when the auxiliary radiation protection portions 104 and 106 are at the non-protecting positions. Moreover, because the auxiliary radiation protection portions 104 and 106 are structured with the same shapes as the auxiliary radiation protection portions 44 and 46 of the above-described first exemplary embodiment, when the auxiliary radiation protection portions 104 and 106 are at the non-protecting positions regardless of which position, the radiation generation source 28B is not blocked by the auxiliary radiation protection portions 104 and 106. Therefore, the above-mentioned usual imaging illustrated in FIG. 11 and tomosynthesis imaging illustrated in FIG. 12 are possible.

In the radiographic imaging device 10 according to the second exemplary embodiment, the auxiliary radiation protection portions 104 and 106 are folded at the side portions 102D and 102E of the main radiation protection portion 102. Therefore, the auxiliary radiation protection portions 104 and 106 can be moved between the protecting positions and the non-protecting positions simply by being folded relative to the main radiation protection portion 102.

In the radiographic imaging device 10 according to the second exemplary embodiment, the auxiliary radiation protection portions 104 and 106 are made movable by a simpler structure—just the third turning shafts 108A and 108B—than the turning mechanism 54 of the radiographic imaging device 10 according to the first exemplary embodiment. Therefore, the structure of the radiographic imaging device 10 may be simplified. Furthermore, in the radiographic imaging device 10 according to the second exemplary embodiment, the stowing mechanism 60 of the radiographic imaging device 10 according to the first exemplary embodiment is not provided. Thus, simplification may be realized furthermore. With the radiography protection unit 100 according to the second exemplary embodiment, the radiographic imaging device 10 that may achieve these operations and effects may be embodied.

Variant Example

The radiographic imaging device and radiography protection unit are described in accordance with a variant example of the second exemplary embodiment, using FIG. 22 to FIG. 25. For the variant example, an example of the radiography protection unit is described in which looseness between the main radiation protection portion and each auxiliary radiation protection portion at the protecting position is effectively reduced.

—Structure of the Radiography Protection Unit—

Figure 22:
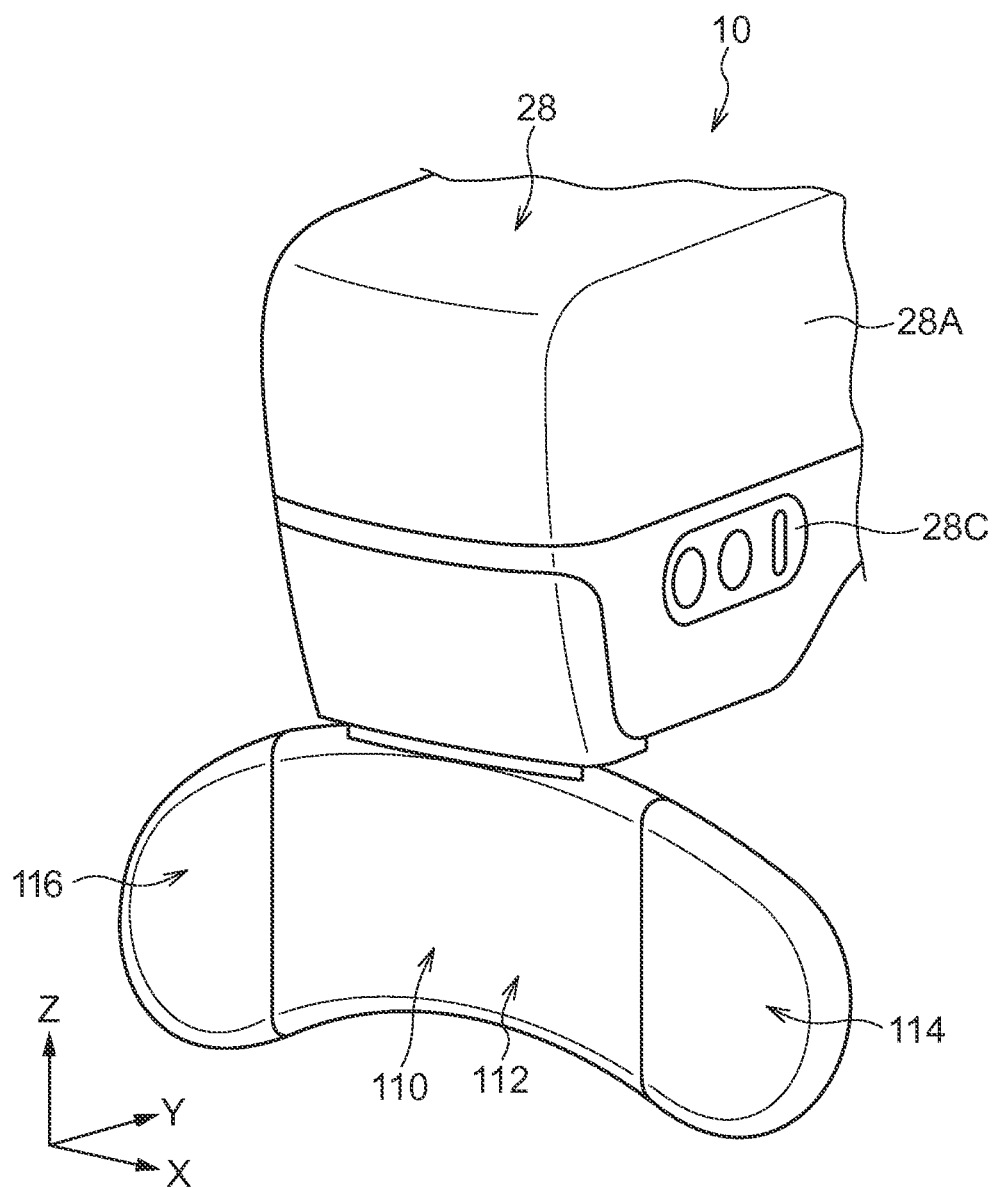
FIG. 22 is a perspective view, corresponding to FIG. 19, of the principal portions of a radiographic imaging device in accordance with a variant example of the second exemplary embodiment, when the auxiliary radiation protection portions are at the protecting positions.

As shown in FIG. 22, the radiographic imaging device 10 according to the variant example is provided with a radiography protection unit 110 that is similar to the radiography protection unit 40 according to the first exemplary embodiment. The radiography protection unit 110 is provided with a main radiation protection portion 112, which is detachably mounted at the radiation irradiation section 28, and auxiliary radiation protection portions 114 and 116, which are disposed at the two left and right side portions of the main radiation protection portion 112. The auxiliary radiation protection portions 114 and 116 shown in FIG. 22 are both set to the protecting positions.

—Structure of the Main Radiation Protection Portion—

Figure 24A:
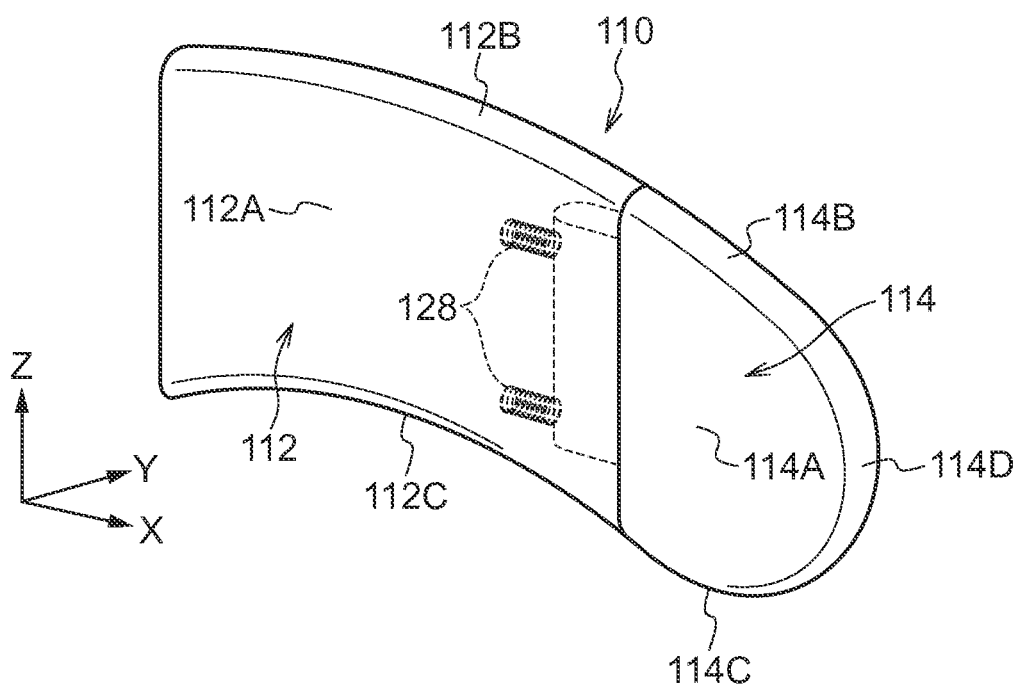
FIG. 24A, FIG. 24B and FIG. 24C are diagrams describing a procedure of changing the protection range of the radiography protection unit shown in FIG. 22 and FIG. 23.
Figure 24B:
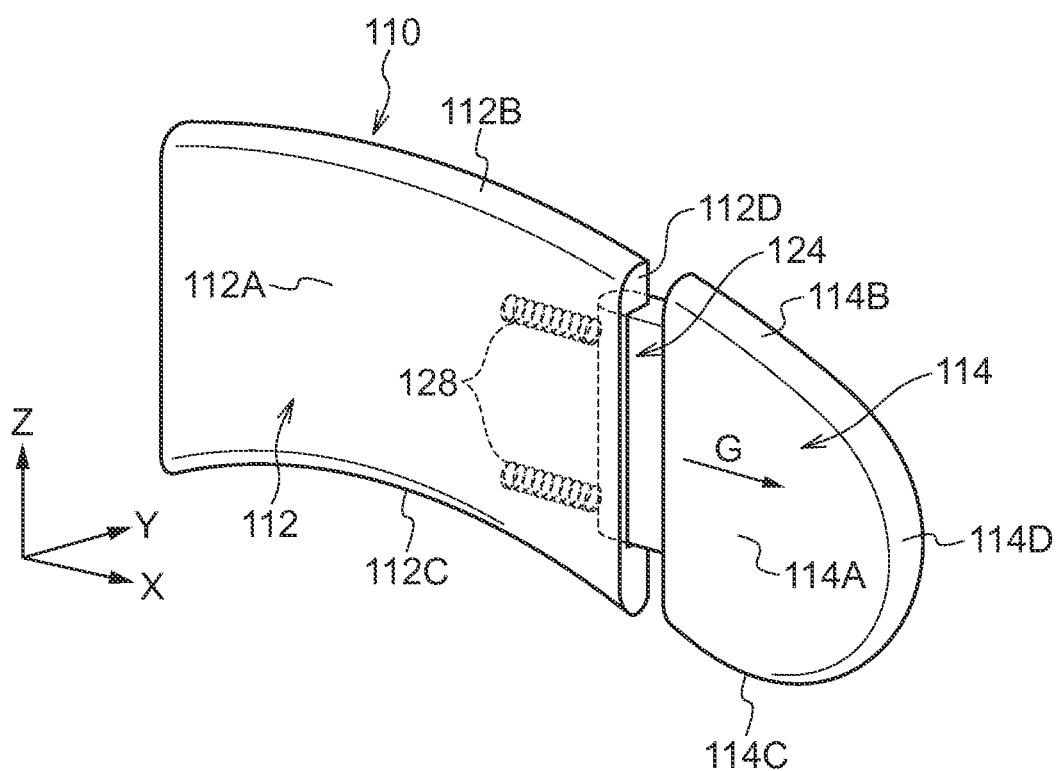
Figure 24C:
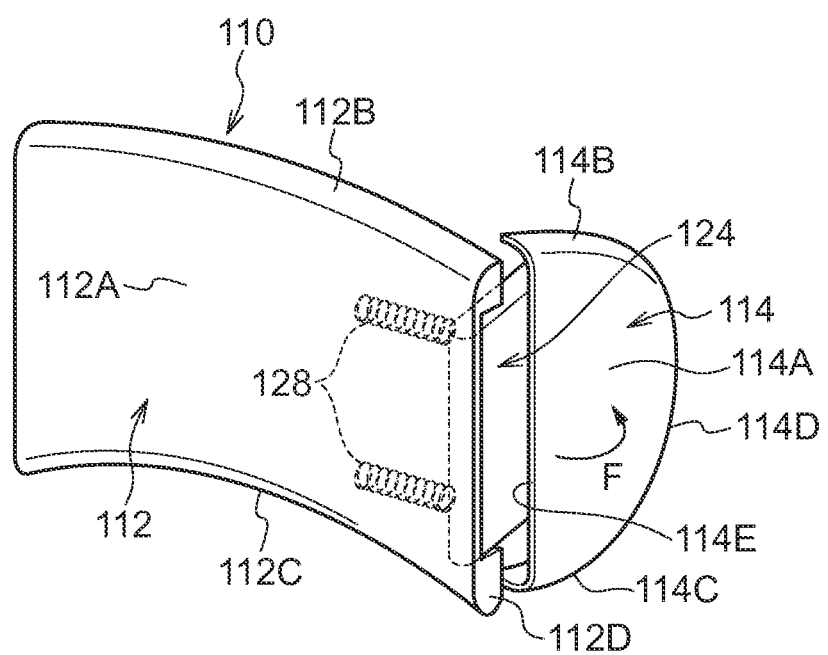

As shown in FIG. 24A to FIG. 24C, similarly to the main radiation protection portion 42 of the first exemplary embodiment, the main radiation protection portion 112 of the radiography protection unit 110 is provided with a protection portion main body 112A that is formed by a plate member including an upper portion 112B, a lower portion 112C, and a side portion 112D (a side portion corresponding to the side portion 42E is not shown). In this case, the protection portion main body 112A is formed in a rectangular shape with the longest direction thereof set to the left-and-right direction (the X direction) as viewed from the test subject side. Although the structure is not described in detail here, the main radiation protection portion 112 is detachably assembled to the radiation irradiation section 28 via a mounting mechanism. The main radiation protection portion 112 is fabricated of the same material as the main radiation protection portion 42 of the radiography protection unit 40.

—Structure of the Auxiliary Radiation Protection Portion—

As shown in FIG. 24A to FIG. 24C, similarly to the auxiliary radiation protection portion 44 of the first exemplary embodiment, the auxiliary radiation protection portion 114 is provided with a protection portion main body 114A that is formed of a plate member in a half-moon shape. The protection portion main body 114A includes an upper portion 114B, a lower portion 114C, and side portions 114D and 114E. That is, the side portion 114E at the side of the protection portion main body 114A is formed as a straight vertical wall, and the opposite side portion 114D is formed in a curved shape that protrudes to the outer side. Descriptions of the respective portions are not given, but the auxiliary radiation protection portion 116 is provided with basically the same structures as the auxiliary radiation protection portion 114 and has mirror symmetry with the auxiliary radiation protection portion 114 about the center line CL (see FIG. 2).

—Moving Mechanism of the Radiography Protection Unit—

Figure 23:
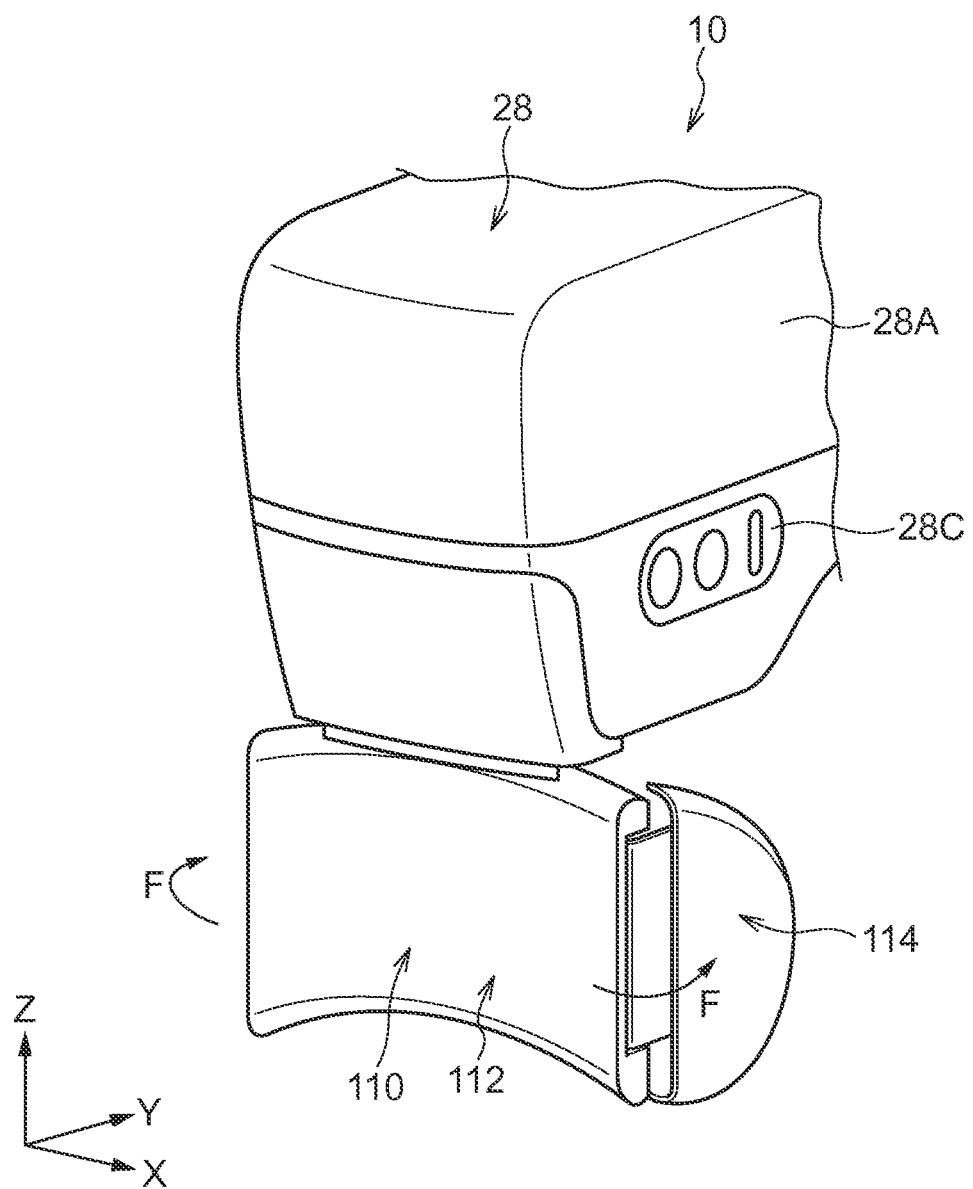
FIG. 23 is a perspective view, corresponding to FIG. 21, of the principal portions of a radiographic imaging device in accordance with the variant example of the second exemplary embodiment, when the auxiliary radiation protection portions are at the non-protecting positions.

As shown in FIG. 23, the radiographic imaging device 10 according to the variant example is equipped with a moving mechanism in the radiography protection unit 110. The moving mechanism enables folding of the auxiliary radiation protection portions 114 and 116 relative to the main radiation protection portion 112 from the protecting positions to the non-protecting positions. That is, the auxiliary radiation protection portions 114 and 116 are each a structure that is movable in the direction of arrow F between the protecting position at the side portion 112D of the main radiation protection portion 112 and the non-protecting position that is disposed at the rearward side of the main radiation protection portion 112.

FIG. 25A and FIG. 25B show the moving mechanism that is provided between the side portion 112D of the main radiation protection portion 112 and the side portion 114E of the auxiliary radiation protection portion 114. This moving mechanism is provided with, as principal structures, a third turning shaft 132, a protecting position accommodation portion 120 including a guiding portion 122, a turning engagement portion 124 including a guided portion 126, and a second resilient member 128. The third turning shaft 132 is a turning shaft that corresponds to the third turning shaft 108A of the second exemplary embodiment. The third turning shaft 132 is provided at the side portion 112D of the main radiation protection portion 112 with the axial direction thereof in a direction along the irradiation axis of the radiation (see FIG. 11 to FIG. 13).

The turning engagement portion 124 is structured integrally with the side portion 114E of the auxiliary radiation protection portion 114, and is structured with a substantially rectangular outline shape in a plan sectional view, with the longest direction thereof in a planar direction of the main radiation protection portion 112 (the X direction) when at the protecting position (the state shown in FIG. 25A). A long hole 130 is provided penetrating through the middle of the turning engagement portion 124. The long axis of the long hole 130 is set to the same direction as the longest direction of the turning engagement portion 124. The third turning shaft 132 penetrates through this long hole 130. When the auxiliary radiation protection portion 114 is moved in the planar direction of the main radiation protection portion 112 (the direction of arrow G shown in FIG. 24B) from the protecting position, the turning engagement portion 124 engages with the third turning shaft 132 and the auxiliary radiation protection portion 114 can be turned to the non-protecting position (in the direction of arrow F shown in FIG. 24C). As shown in FIG. 25A, the guided portion 126 is provided at the rear face side of the turning engagement portion 124. When the auxiliary radiation protection portion 114 moves in the direction of arrow G (when a protecting state at the protecting position is disengaged), the guided portion 126 touches against and is guided by the guiding portion 122. The guided portion 126 is structured by a tapered surface whose dimension decreases, in the plan sectional view, from the auxiliary radiation protection portion 114 side thereof to the main radiation protection portion 112 side thereof.

The protecting position accommodation portion 120 includes a recess that opens to the side at which the auxiliary radiation protection portion 114 is disposed, in the plan sectional view. The protecting position accommodation portion 120 is structured integrally with the side portion 112D of the main radiation protection portion 112. The protecting position accommodation portion 120 accommodates and retains the auxiliary radiation protection portion 114 when the same is at the protecting position. The guiding portion 122 is provided at a portion that corresponds with the guided portion 126, which portion is an inner wall of the protecting position accommodation portion 120. The guiding portion 122 guides the turning engagement portion 124 in the direction of arrow G.

One end of the second resilient member 128 is joined to the main radiation protection portion 112, and the other end is joined to the turning engagement portion 124. The second resilient member 128 provides actions to direct the turning engagement portion 124 into the protecting position accommodation portion 120, and to urge the guided portion 126 of the turning engagement portion 124 in a direction causing the guided portion 126 to touch the guiding portion 122 of the protecting position accommodation portion 120 (the direction of arrow H in FIG. 25A). As an example, a coil spring is used as the second resilient member 128. In this case, the second resilient member 128 is provided in a plural number in the up-and-down direction.

Although not shown in the drawings, a similar moving mechanism is provided between the auxiliary radiation protection portion 116 and the side portion of the main radiation protection portion 112 that is at the opposite side of the main radiation protection portion 112 from the side at which the side portion 112D is disposed.

Operation and Effects of the Variant Example

In the radiographic imaging device 10 according to the present variant example, as shown in FIG. 25A and FIG. 25B, the turning engagement portion 124 is provided at the auxiliary radiation protection portion 114. When the auxiliary radiation protection portion 114 is moved from the protecting position shown in FIG. 24A and FIG. 25A in the planar direction of the main radiation protection portion 112 shown in FIG. 24B (the direction of arrow G), the turning engagement portion 124 is engaged with the third turning shaft 132. When this engagement is made, the auxiliary radiation protection portion 114 can be turned to the non-protecting position as shown in FIG. 24C and FIG. 25B.

At the side portion 112D of the main radiation protection portion 112, the guiding portion 122 is provided at the protecting position accommodation portion 120, and the guiding portion 122 guides the turning engagement portion 124 in the planar direction (the direction of arrow G). Correspondingly, at the side portion 114E of the auxiliary radiation protection portion 114, the guided portion 126 is provided at the turning engagement portion 124. When the auxiliary radiation protection portion 114 is moved in the planar direction, the guided portion 126 touches and is guided by the guiding portion 122. The second resilient member 128 is also provided, which urges the guided portion 126 in the direction to touch against the guiding portion 122. Therefore, when the auxiliary radiation protection portion 114 is at the protecting position, because the second resilient member 128 is urging in the direction such that the guiding portion 122 and the guided portion 126 touch together, looseness between the guiding portion 122 and the guided portion 126 is effectively reduced. Therefore, the auxiliary radiation protection portion 114 may be securely retained at the main radiation protection portion 112. The same operations and effects may be realized between the main radiation protection portion 112 and the auxiliary radiation protection portion 116 at the protecting position. With the radiography protection unit 110 according to the present variant example, the radiographic imaging device 10 that may achieve these operations and effects may be embodied.

Alternative Embodiments

The present invention has been described above using a number of exemplary embodiments and a number of variant examples, but the present invention is not limited by these embodiments and examples, and numerous modifications may be made within a scope not deviating from the spirit of the invention. For example, the present invention may be applied to a radiography protection unit in which an auxiliary radiation protection portion is provided at one side portion of a main radiation protection portion. In this case, it is preferable if the auxiliary radiation protection portion is disposed at a side portion of the main radiation protection portion that is at a side that corresponds with a control section disposed at a side portion of the radiation irradiation section 28 (for example, a portion corresponding to the reference symbol 28C in FIG. 1). That is, the auxiliary radiation protection portion may be moved from a protecting position to a non-protecting position or a stowed position when operability of the control section would be impaired.

As a further example, the present invention is applicable both to mammography devices with tomosynthesis functions and to mammography devices that perform imaging in which a radiation source is inclined from the vertical axis (for example, the mammography device with a stereo imaging function illustrated in JP-A Nos. 2009-207561).

What is claimed is:
1. A radiographic imaging device comprising:
an imaging platform that includes an imaging surface on which a breast of a test subject is to be rested;
a radiation irradiation section that is disposed to face the imaging surface and irradiates radiation at the imaging surface;
a main radiation protection portion that is disposed at a side of a region between the radiation irradiation section and the imaging surface at which side the test subject is disposed, and that protects the test subject from the radiation;
a first turning shaft that is provided at a side portion of the main radiation protection portion, an axial direction of the first turning shaft being a direction along an upper edge of the main radiation protection portion; and
an auxiliary radiation protection portion that is firstly turned about the first turning shaft toward an upper edge side of the main radiation protection portion such that the auxiliary radiation protection portion is located at a non-protecting position,
wherein:
in a case in which tomosynthesis imaging is performed by turning the radiation irradiation section to left and right relative to the imaging surface, the auxiliary radiation protection portion is located at a protecting position at which the auxiliary radiation protection portion is disposed at a side portion of the main radiation protection portion, and
in a case in which two-dimensional imaging is performed in which an irradiation angle of radiation with respect to the imaging surface is set substantially to a perpendicular angle, the auxiliary radiation protection portion is set to the non-protecting position, and
the non-protecting position is located at a plane that is extended along left and right directions of the test subject and along a direction from a test subject side toward a back side of the radiographic imaging device.

2. The radiographic imaging device according to claim 1, wherein the auxiliary radiation protection portion comprises:
a plate-shaped protection portion main body; and
a reinforcing member that reinforces a joining location between the protection portion main body and the first turning shaft.

3. The radiographic imaging device according to claim 1, wherein the auxiliary radiation protection portion is provided at each of two side portions of the main radiation protection portion.

4. The radiographic imaging device according to claim 1, wherein the main radiation protection portion is detachably provided at a lower end portion of the radiation irradiation section.

5. The radiographic imaging device according to claim 1, wherein, as viewed from the side at which the test subject is disposed, a boundary location between the main radiation protection portion and the auxiliary radiation protection portion is specified to be between an irradiation region of the radiation and a side face of the radiation irradiation section.

6. The radiographic imaging device according to claim 1, wherein side portions of the main radiation protection portion are both formed in curved shapes protruding to outer sides of the main radiation protection portion, wherein a side portion at an inner side of the auxiliary radiation protection portion is formed in a curved shape that is recessed so as to touch against one of the side portions of the main radiation protection portion, and wherein a side portion at an outer side of the auxiliary radiation protection portion is formed in a curved shape that protrudes to an outer side.

7. The radiographic imaging device according to claim 1, wherein a second turning shaft is provided at a side end portion of the first turning shaft, an axial direction of the second turning shaft being a direction that intersects the first turning shaft, and wherein after the auxiliary radiation protection portion is turned to the non-protecting position, the auxiliary radiation protection portion is secondly turned about the second turning shaft such that a portion of the auxiliary radiation protection portion overlaps with a rear face of the main radiation protection portion as viewed from a rear face side of the main radiation protection portion, and the auxiliary radiation protection portion is stowed.

8. The radiographic imaging device according to claim 7, wherein:

the auxiliary radiation protection portion turns about the second turning shaft between the non-protecting position and a stowed position, which is at a rear face side of the main radiation protection portion relative to the non-protecting position.

9. The radiographic imaging device according to claim 8, further comprising a turning position retention mechanism that retains a turning position of the auxiliary radiation protection portion at each of the non-protecting position and the stowed position.

10. The radiographic imaging device according to claim 7, wherein in the event that the auxiliary radiation protection portion is secondly turned about the second turning shaft such that the auxiliary radiation protection portion comes close to the rear face of the main radiation protection portion, the auxiliary radiation protection portion does not overlap with an irradiation axis of the radiation from the radiation irradiation section toward the imaging surface.

11. The radiographic imaging device according to claim 7, wherein the portion of the auxiliary radiation protection portion overlaps with the rear face of the main radiation protection portion and the auxiliary radiation protection portion is stowed, in a case in which imaging is not performed.

12. A radiography protection unit comprising:
a main radiation protection portion and an auxiliary radiation protection portion according to claim 1; wherein:
the auxiliary radiation protection portion is disposed at a side portion of the main radiation protection portion, and
the main radiation protection portion and the auxiliary radiation protection portion are provided at a radiation irradiation device.

13. A radiographic imaging device comprising:
an imaging platform that includes an imaging surface on which a breast of a test subject is to be rested;
a radiation irradiation section that is disposed to face the imaging surface and irradiates radiation at the imaging surface;

a main radiation protection portion that is disposed at a side of a region between the radiation irradiation section and the imaging surface at which side the test subject is disposed, and that is adapted to protect the test subject from the radiation; and a first turning shaft that is provided at a side portion of the main radiation protection portion, an axial direction of the first turning shaft being a direction along an upper edge of the main radiation protection portion; and a second turning shaft that is provided at a side end portion of the first turning shaft, an axial direction of the second turning shaft being a direction that intersects the first turning shaft, an auxiliary radiation protection portion that is stowed at a space, the space being formed at a rear side of the main radiation protection portion and the rear side being opposite to a side at which the test subject is disposed, by the auxiliary radiation protection portion being firstly turned about the first turning shaft toward an upper edge side of the main radiation protection portion and being secondly turned about the second turning shaft toward the rear side of the main radiation protection portion such that a portion of the auxiliary radiation protection portion overlaps with a rear face of the main radiation protection portion, wherein:

in a case in which tomosynthesis imaging is performed by turning the radiation irradiation section to left and right relative to the imaging surface, the auxiliary radiation protection portion is disposed at a side portion of the main radiation protection portion, and in a case in which two-dimensional imaging is performed in which an irradiation angle of radiation with respect to the imaging surface is set substantially to a perpendicular angle, the auxiliary radiation protection portion is set to a non-protective position by the first turning, and the non-protecting position is located at a plane that is extended along left and right directions of the test subject and along a direction from a test subject side toward a back side of the radiographic imaging device.

14. The radiographic imaging device according to claim 13, further comprising a turning position retention mechanism that retains a turning position of the auxiliary radiation protection portion at each of the non-protecting position and the stowed position.

15. The radiographic imaging device according to claim 13, wherein the auxiliary radiation protection portion comprises:
a plate-shaped protection portion main body; and
a reinforcing member that reinforces a joining location between the protection portion main body and the first turning shaft.

16. The radiographic imaging device according to claim 13, wherein the auxiliary radiation protection portion is provided at each of two side portions of the main radiation protection portion.

17. The radiographic imaging device according to claim 13, wherein the main radiation protection portion is detachably provided at a lower end portion of the radiation irradiation section.

18. The radiographic imaging device according to claim 13, wherein, as viewed from the side at which the test subject is disposed, a boundary location between the main radiation protection portion and the auxiliary radiation protection portion is specified to be between an irradiation region of the radiation and a side face of the radiation irradiation section.

19. The radiographic imaging device according to claim 13, wherein in the event that the auxiliary radiation protection portion is secondly turned about the second turning shaft such that the auxiliary radiation protection portion comes close to the rear face of the main radiation protection portion, the auxiliary radiation protection portion does not overlap with an irradiation axis of the radiation from the radiation irradiation section toward the imaging surface.

20. The radiographic imaging device according to claim 13,
wherein side portions of the main radiation protection portion are both formed in curved shapes protruding to outer sides of the main radiation protection portion,
wherein a side portion at an inner side of the auxiliary radiation protection portion is formed in a curved shape that is recessed so as to touch against one of the side portions of the main radiation protection portion, and
wherein a side portion at an outer side of the auxiliary radiation protection portion is formed in a curved shape that protrudes to an outer side.

21. The radiographic imaging device according to claim 13, wherein the portion of the auxiliary radiation protection portion overlaps with the rear face of the main radiation protection portion, in a case in which imaging is not performed.

22. A radiography protection unit comprising:
a main radiation protection portion and an auxiliary radiation protection portion according to claim 13; wherein:
the auxiliary radiation protection portion is disposed at a side portion of the main radiation protection portion, and
the main radiation protection portion and the auxiliary radiation protection portion are provided at a radiation irradiation device.

* * * * *